United States Patent [19]
Zavracky et al.

[11] Patent Number: 5,751,261
[45] Date of Patent: May 12, 1998

[54] CONTROL SYSTEM FOR DISPLAY PANELS

[75] Inventors: Matthew Zavracky, North Attleboro; Vic Odryna, Acton; Barry Mansell, Groton, all of Mass.

[73] Assignee: Kopin Corporation, Taunton, Mass.

[21] Appl. No.: 106,416

[22] Filed: Aug. 13, 1993

Related U.S. Application Data

[63] Continuation-in-part of Ser. No. 971,399, Nov. 4, 1992, abandoned, which is a continuation-in-part of Ser. No. 944,207, Sep. 11, 1992, which is a continuation-in-part of Ser. No. 823,858, Jan. 22, 1992, abandoned, and Ser. No. 872,297, Apr. 22, 1992, which is a continuation-in-part of Ser. No. 839,241, Feb. 20, 1992, abandoned, which is a continuation-in-part of Ser. No. 636,602, Dec. 31, 1990, Pat. No. 5,206,749.

[51] Int. Cl.$^6$ ............................................. G09G 3/20
[52] U.S. Cl. ........................................ 345/55; 345/99
[58] Field of Search .............................. 345/207, 55, 58, 345/87, 89, 101, 63, 99, 100, 102, 132, 127; 348/777, 776

[56] References Cited

U.S. PATENT DOCUMENTS

| | | | |
|---|---|---|---|
| 3,807,037 | 4/1974 | Fischer | 437/59 |
| 3,869,646 | 3/1975 | Kirton et al. | 315/246 |
| 3,904,924 | 9/1975 | Hilsum et al. | 345/81 |
| 3,947,842 | 3/1976 | Hilsum et al. | 345/81 |
| 3,972,040 | 7/1976 | Hilsum et al. | 345/76 |
| 4,127,792 | 11/1978 | Nakata | 313/500 |
| 4,137,481 | 1/1979 | Hilsum et al. | 313/503 |
| 4,143,297 | 3/1979 | Fischer | 313/502 |
| 4,266,223 | 5/1981 | Frame | 345/80 |
| 4,339,514 | 7/1982 | Biber | 430/7 |
| 4,399,015 | 8/1983 | Endo et al. | 204/192.26 |
| 4,409,724 | 10/1983 | Tasch, Jr. et al. | 437/19 |
| 4,416,514 | 11/1983 | Plummer | 359/53 |
| 4,470,667 | 9/1984 | Okubo et al. | 359/67 |
| 4,600,274 | 7/1986 | Morozumi | 359/58 |

(List continued on next page.)

FOREIGN PATENT DOCUMENTS

| | | |
|---|---|---|
| 0 151 508 | 8/1985 | European Pat. Off. . |
| 0 241 562 | 10/1987 | European Pat. Off. . |
| 0 313 331 | 4/1989 | European Pat. Off. . |
| 0 352 636 | 1/1990 | European Pat. Off. . |
| 62271569 | 11/1987 | Japan . |
| 63055529 | 10/1988 | Japan . |
| 1038727 | 9/1989 | Japan . |
| 1280795 | 11/1989 | Japan . |
| 2216120 | 8/1990 | Japan . |
| 3096918 | 7/1991 | Japan . |
| 7020824 | 1/1995 | Japan . |
| WO 88/09268 | 12/1988 | WIPO . |
| 93/15589 | 8/1993 | WIPO . |

OTHER PUBLICATIONS

Yamano et al. "The 5-Inch Size Full Clor Liquid Crystal Television Addressed By Amorphous Silicon Thin Film Transistors" IEEE Transactions of Consumer Electronics, CE-31 No. 1 (Feb. 1985), pp. 39-46.

(List continued on next page.)

*Primary Examiner*—Curtis Kuntz
*Assistant Examiner*—Vivian Chang
*Attorney, Agent, or Firm*—Hamilton, Brook, Smith & Reynolds, P.C.

[57] ABSTRACT

A control apparatus for an active matrix liquid crystal display device is fabricated with the active matrix as a single integrated SOI circuit. The control apparatus and the active matrix are lifted from a silicon substrate and transferred to a glass substrate as a single piece. The control apparatus comprises a video interface, a column driver, and dual row drivers. The video interface operates the active matrix as a multiple-frequency scanning display device. The polarities of the display pixels are reversed on every frame by a polarity switch coupled to a video signal amplifier. The control apparatus further comprises sensors for generating a gray-scale feedback signal to adjust the gain of the video amplifier. User control of the display is provided by a user interface.

20 Claims, 14 Drawing Sheets

U.S. PATENT DOCUMENTS

| | | | |
|---|---|---|---|
| 4,610,509 | 9/1986 | Sorimachi et al. | 359/68 |
| 4,653,862 | 3/1987 | Morozumi | 359/58 |
| 4,716,403 | 12/1987 | Morozumi | 345/88 |
| 4,717,606 | 1/1988 | Hale | 428/1 |
| 4,786,964 | 11/1988 | Plummer et al. | 348/270 |
| 4,797,667 | 1/1989 | Dolinar et al. | 345/76 |
| 4,808,501 | 2/1989 | Chiulli | 430/7 |
| 4,852,032 | 7/1989 | Matsuda et al. | 364/708 |
| 4,886,343 | 12/1989 | Johnson | 359/53 |
| 4,917,465 | 4/1990 | Conner et al. | 359/41 |
| 4,929,884 | 5/1990 | Bird et al. | 323/313 |
| 4,977,350 | 12/1990 | Tanaka et al. | 313/505 |
| 4,980,308 | 12/1990 | Hayashi et al. | 437/41 |
| 5,032,007 | 7/1991 | Silverstein et al. | 359/53 |
| 5,032,831 | 7/1991 | Kuijk | 345/91 |
| 5,053,765 | 10/1991 | Sonehara et al. | 340/815.31 |
| 5,093,738 | 3/1992 | Watanabe et al. | 359/68 |
| 5,099,345 | 3/1992 | Kozaki et al. | 359/93 |
| 5,250,937 | 10/1993 | Kikuo | 345/101 |
| 5,307,085 | 4/1994 | Nakamura | 345/99 |

OTHER PUBLICATIONS

Tanaka et al., "Luminance Improvement of Blue–and White– Emitting SRS TFEL Devices by Annealing In Ar–S Atmosphere," 1991 International Display Research Conference, CH–3071–8/91/0000–0137 (IEEE 1991).

Vanfleteren et al., "Evaluation of a 64x64 CdSe TFT Addressed ACTFEL display Demonstrator," 1991 International Display Research Conference, CH–3071–8/91/0000–0134 (IEEE 1991).

Singh et al., "Effect of Bulk Space Charge on the Current and Luminescence Characteristics of ZnS:Mn ACTFEL Display Devices", 1991 International Display Research Conference, CH–3071–8/91/0000–0130 (IEEE 1991).

Laakso et al., "A 9 Inch Diagonal, Compact, Multicolor TFEL Display," 1991 International Display Research Conference. CH–3071–8/91/0000–0043 (IEEE 1991).

Vanfleteren et al., "Design of a Prototype Active Matrix CdSe TFT Addressed El Display", Laboratory of Electronics, Ghent State University, Belgium and Lohja–Finlux, Finland, 216–219.

D.N. Schmidt, Proceedings of the Fourth Annual International Symposium on "Silicon–on Insulator Technologoy and Devices", 90–6: 21–47.

J. Hurd, "Color Electroluminescent Display Development", *Flat Information Display–1990*, 1–10.

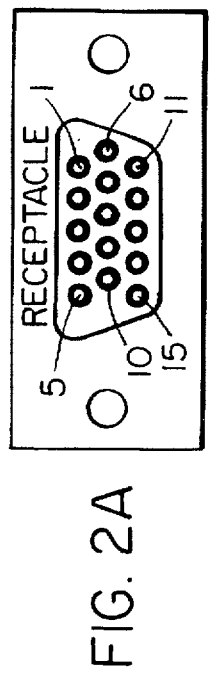

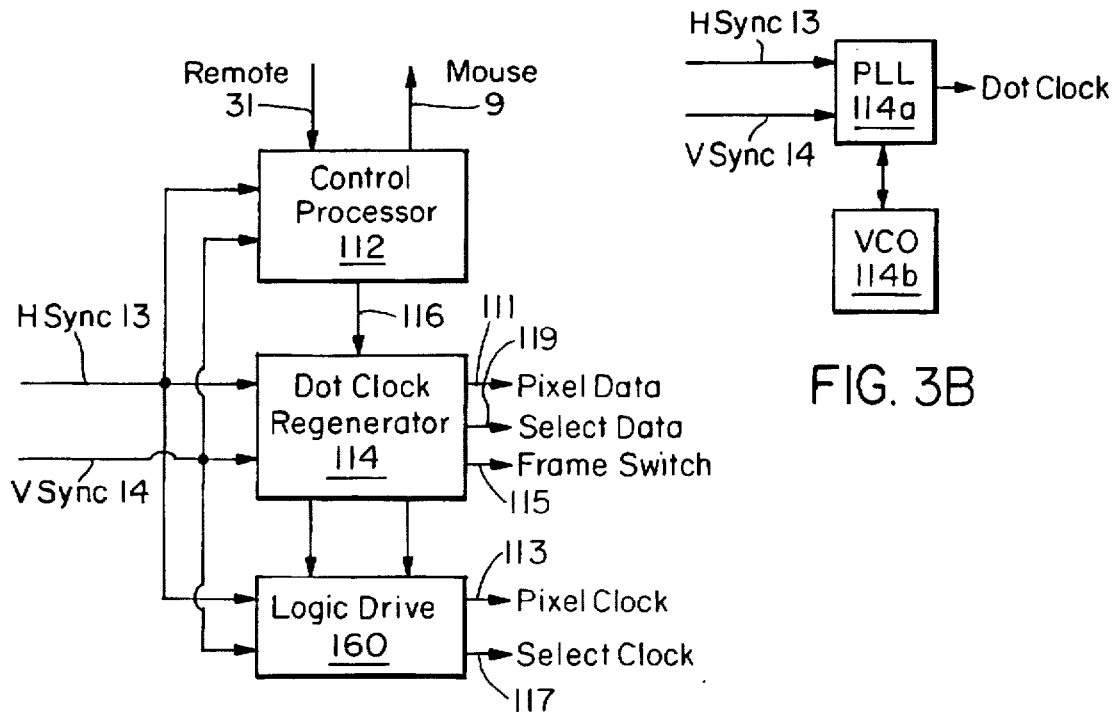
FIG. 3A
FIG. 3B
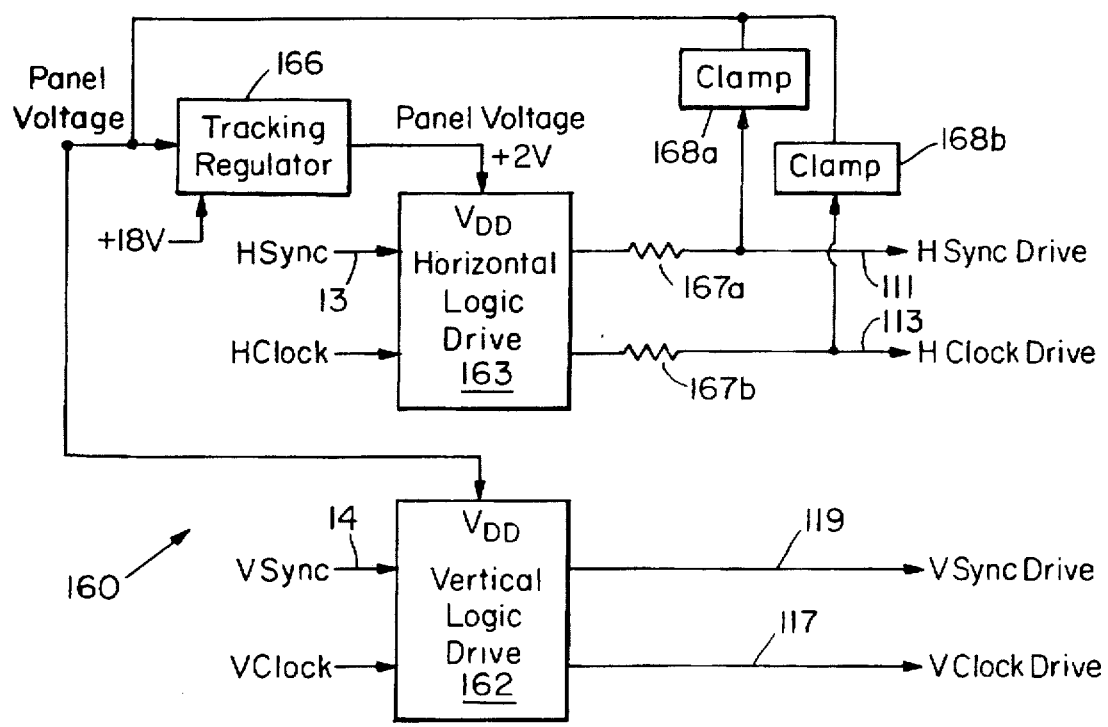
FIG. 3C

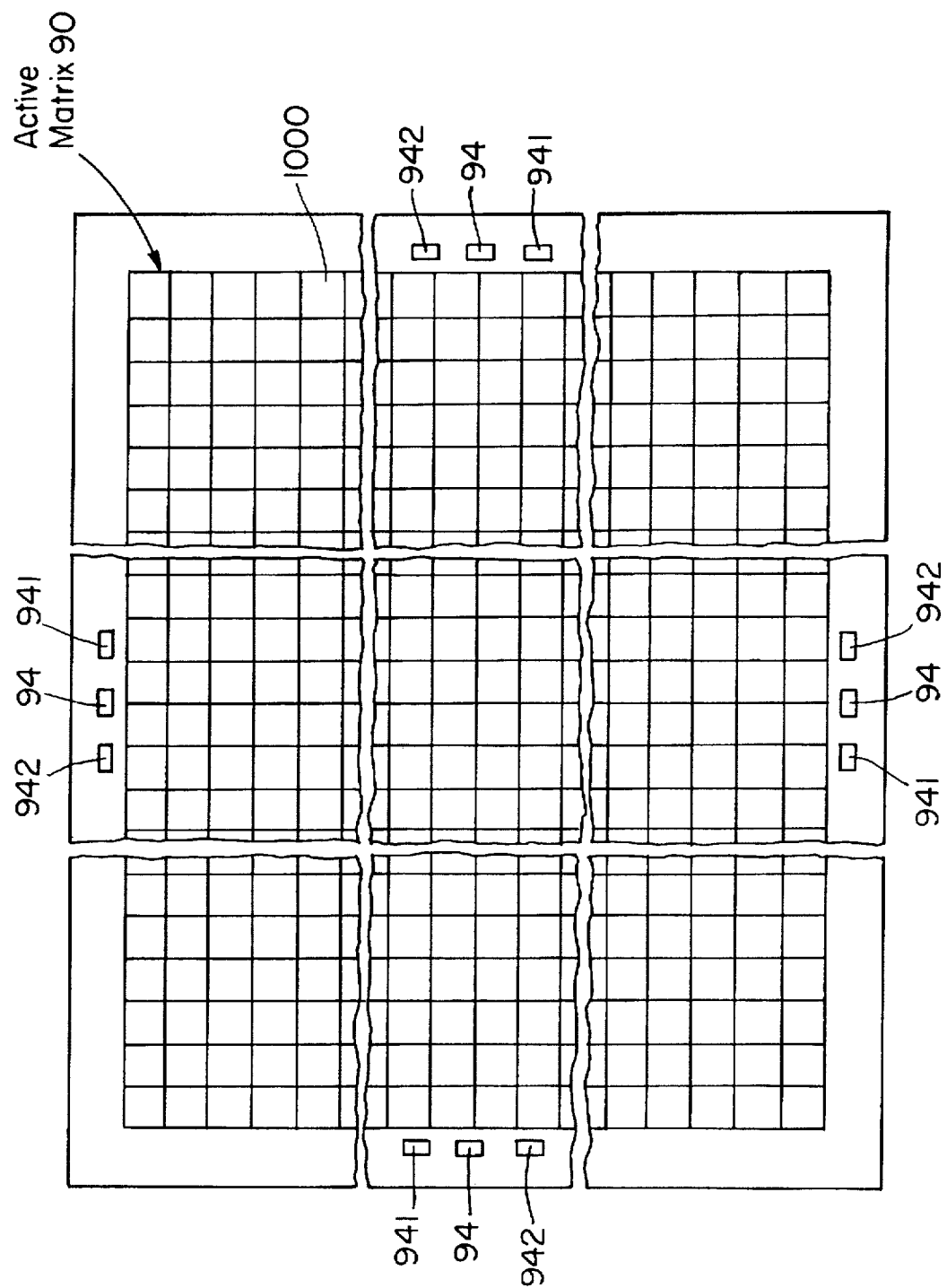

Active Matrix Region 90

Active Matrix Region 90

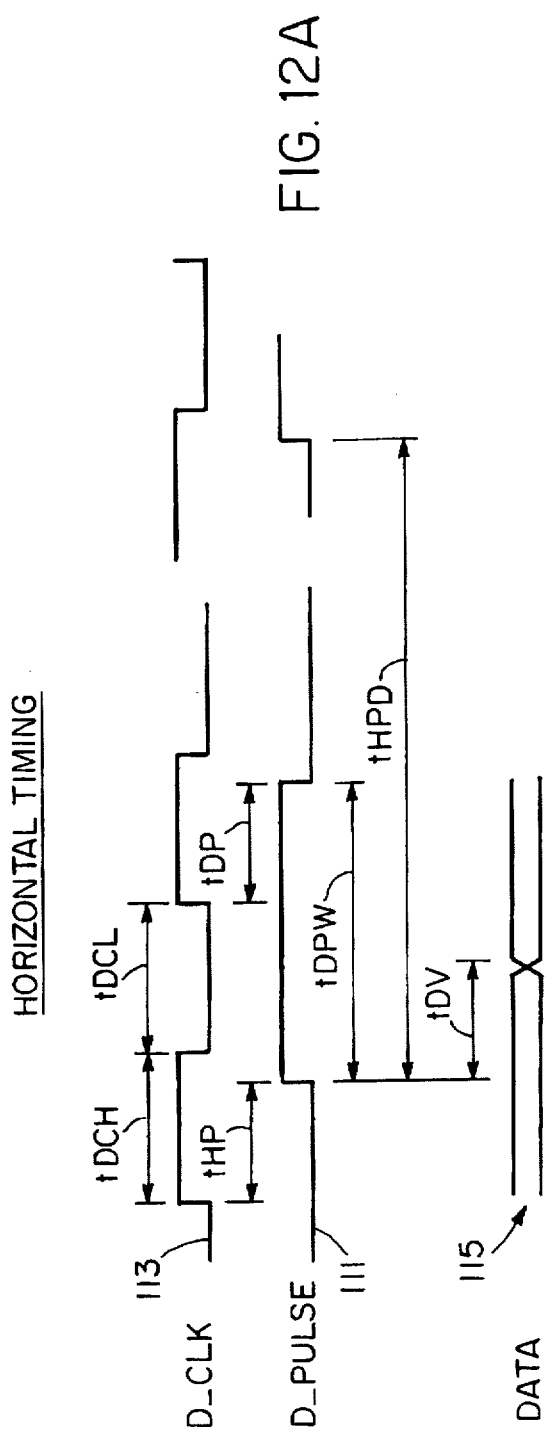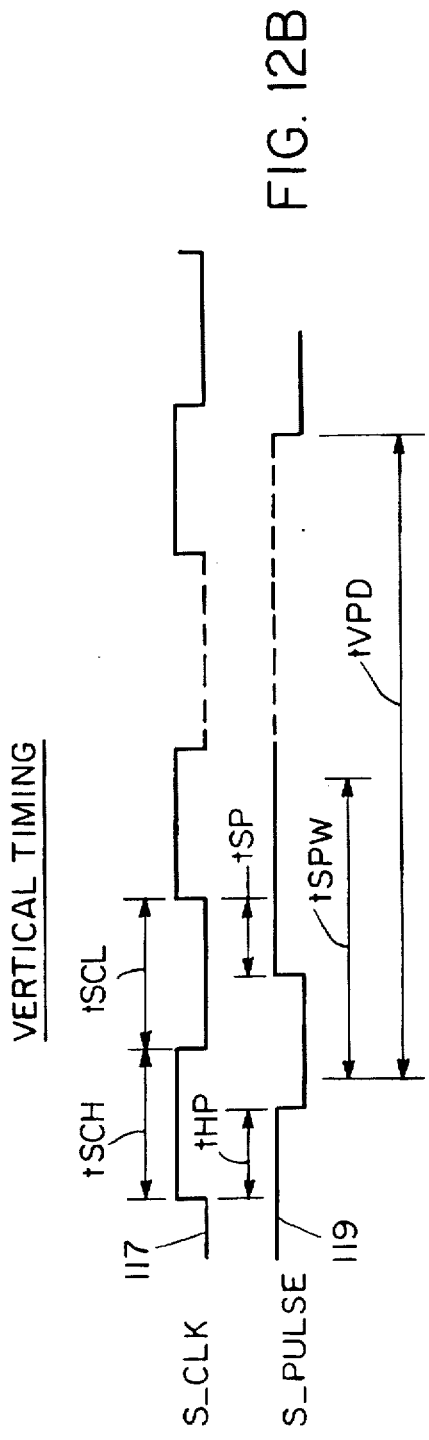

CONTROL SYSTEM FOR DISPLAY PANELS

RELATED APPLICATION

This application is a Continuation-In-Part of U.S. patent application, Ser. No. 07/971,399 filed Nov. 4, 1992, now abandoned, which is a Continuation-In-Part of U.S. patent application, Ser. No. 07/944,207 filed on Sep. 11, 1992, now allowed, which is also a Continuation-In-Part of Ser. No. 07/823,858 filed on Jan. 22, 1992, now abandoned, and of Ser. No. 07/872,297, filed Apr. 22, 1992, now allowed which is a Continuation-In-Part of U.S. patent application, Ser. No. 07/839,241 filed Feb. 20, 1992, now abandoned, which is a Continuation-In-Part of U.S. patent application, Ser. No. 07/636,602 filed Dec. 31, 1990, now U.S. Pat. No. 5,206,749, all of which are incorporated herein by reference.

BACKGROUND OF THE INVENTION

Flat-panel displays are being developed which utilize liquid crystals or electroluminescent materials to produce high quality images. These displays are expected to supplant cathode ray tube (CRT) technology and provide a more highly defined television picture. The most promising route to large-scale high-quality liquid crystal displays (LCDs), for example, is the active-matrix approach in which thin-film transistors (TFTs) are co-located with LCD pixels. The primary advantage of the active matrix approach using TFTs is the elimination of cross-talk between pixels, and the excellent gray scale that can be attained with TFT-compatible LCDs.

Flat panel displays employing LCDs generally include five different layers: a white light source, a first polarizing filter that is mounted on one side of a circuit panel on which the TFTs are arrayed to form pixels, a filter plate containing at least three primary colors arranged into pixels, and finally a second polarizing filter. A volume between the circuit panel and the filter plate is filled with a liquid crystal material. This material will rotate the polarization of light when an electric field is applied across the liquid crystal material between the circuit panel and a ground affixed to the filter plate. Thus, when a particular pixel of the display is turned on, the liquid crystal material rotates polarized light being transmitted through the liquid crystal material so the rotated polarized light will pass through the second polarizing filter.

The primary approach to TFT formation over the large areas required for flat panel displays has involved the use of amorphous silicon, which has previously been developed for large-area photovoltaic devices. Although the TFT approach has proven to be feasible, the use of amorphous silicon compromises certain aspects of the panel performance. For example, amorphous silicon TFTs lack the frequency response needed for large area displays due to the low electron mobility inherent in amorphous material. Thus the use of amorphous silicon limits display speed, and is also unsuitable for the fast logic needed to drive the display.

Owing to the limitations of amorphous silicon, other alternative materials include polycrystalline silicon, or laser recrystallized silicon. These materials are limited as they use silicon that is already on glass, which generally restricts further circuit processing to low temperatures.

A continuing need exists for systems and methods of controlling pixel of panel displays having the desired speed and providing for ease, and reduced cost, of fabrication.

SUMMARY OF THE INVENTION

The invention is a control system for an active matrix liquid crystal display panel. A control apparatus is fabricated with the active matrix as a monolithic SOI structure. After the SOI structure is fabricated in a thin film layer of single crystal or substantially single crystal silicon on a silicon substrate, the structure is removed from the silicon substrate using a lift-off process and transferred to a glass substrate as a single substrate. The single structure provides improved processing speeds and the fabrication process reduces the difficulty and cost of manufacturing display panels. In a particular preferred embodiment, the display panel is adapted for use in a standard 35 mm slide projector.

In a preferred embodiment, a control apparatus for a liquid crystal display device comprises a video interface, a left select scanner, a right select scanner, a video polarity network, a data scanner, and a transmission gate. The video interface converts video signals from a video source into active matrix control signals. In response to the active matrix control signals, the left and right select scanners simultaneously drive opposite sides of the matrix select lines. The video polarity network inverts the polarity of the video signals on each successive video frame. A preferred embodiment employs either column inversion or frame inversion techniques. In particular, a column inversion technique is used where the polarity of the even columns is opposite to the polarity of the odd columns on any given video frame. In response to the active matrix control signals, the data scanner triggers the transmission gate to drive the active matrix columns with the even and the odd column signals.

The data scanner comprises an odd-column shift register array and an even-column shift register array. The odd column array triggering an odd column array of the transmission gate and the even column array triggering an even column array of the transmission gate. The odd and even column arrays of the transmission gate drive respective columns of the active matrix.

An encoder may be coupled between the video source and the video polarity network. The encoder generating a superposed analog video signal from a video source Red-Green-Blue (RGB) data signal. The RGB data signal can be mapped to a superposed color analog signal. The RGB data signal can also be mapped to a gray-scale analog signal. Preferably, the encoder can map to either of the color or gray-scale signal in response to a control signal.

In a preferred embodiment, the control apparatus adjusts the gray-scale video signal level to compensate for changes in the transmittance of the liquid crystal material. At least one sensor is fabricated within the SOI structure. A temperature sensor can be used to generate a data signal in response to the temperature of the active matrix. A light sensor can be used to generate a data signal in response to the light transmittance of the liquid crystal material. The sensor can include at least one real-time light sensor at least one real-time temperature sensor, or a combination of light sensors and temperature sensors. The sensor data is processed by a light meter or temperature measurer, which generates a feedback signal in response to the sensor data. An amplifier gain is adjusted by the feedback signal, the amplifier amplifying the video signal by the gain. The gain may be linear or nonlinear.

If light sensors are used, a light transmittance curve for the liquid crystal material must be established. A light sensor is provided that generates a signal representing light transmittance through a black pixel. Another light sensor is provided that generates a signal representing light transmittance through a white pixel. The black and white pixel signals can be generated by permanently connecting one pixel light sensor to a DC voltage and the other pixel light sensor to ground. The black and white pixel light sensors define the end points of the active matrix transmittance curve.

In a preferred embodiment, the video source generates a video signal having variable synchronization frequencies. The active matrix display has a fixed pixel resolution. The video interface generates a dot clock signal from the variable synchronization frequencies for driving the display at the fixed resolution. The video interface allows the display panel to function as a multiple-frequency scanning display device.

The video interface comprises a control processor and dot clock regenerator. The control processor is responsive to video mode changes on the video signal as reflected by changes in the synchronization signals. In response to mode changes, the control processor signals the dot clock regenerator. The dot clock regenerator is responsive to the control processor signal. The dot clock regenerator comprises a digitally programmable phase-locked loop that tracks changes on the synchronization frequencies such that the dot clock signal is centered over the correct pixel and does not drift. The video interface providing compatibility with Video Graphics Array (VGA) adapter and Apple™ video signals.

BRIEF DESCRIPTION OF THE DRAWINGS

The above, and other features of the invention including various novel details of construction and combination of parts, will now be more particularly described with reference to the accompanying drawings. It will be understood that the particular display device and the methods used in fabricating the display device which embody the invention are shown by way of illustration only and not as a limitation of the invention. The principle features of this invention can be employed in various embodiments without departing from the scope of the invention.

FIGS. 2a–2d illustrate preferred video signal connections to a computer video source.

FIGS. 3a–3c an schematic block diagrams of a preferred video interface 110 of FIG. 1.

FIGS. 6a–6c are views of the display device showing a preferred light sensor arrangement.

FIGS. 12A–12B are timing diagrams for a particular preferred embodiment of the invention.

DETAILED DESCRIPTION OF THE INVENTION

Figure 1:
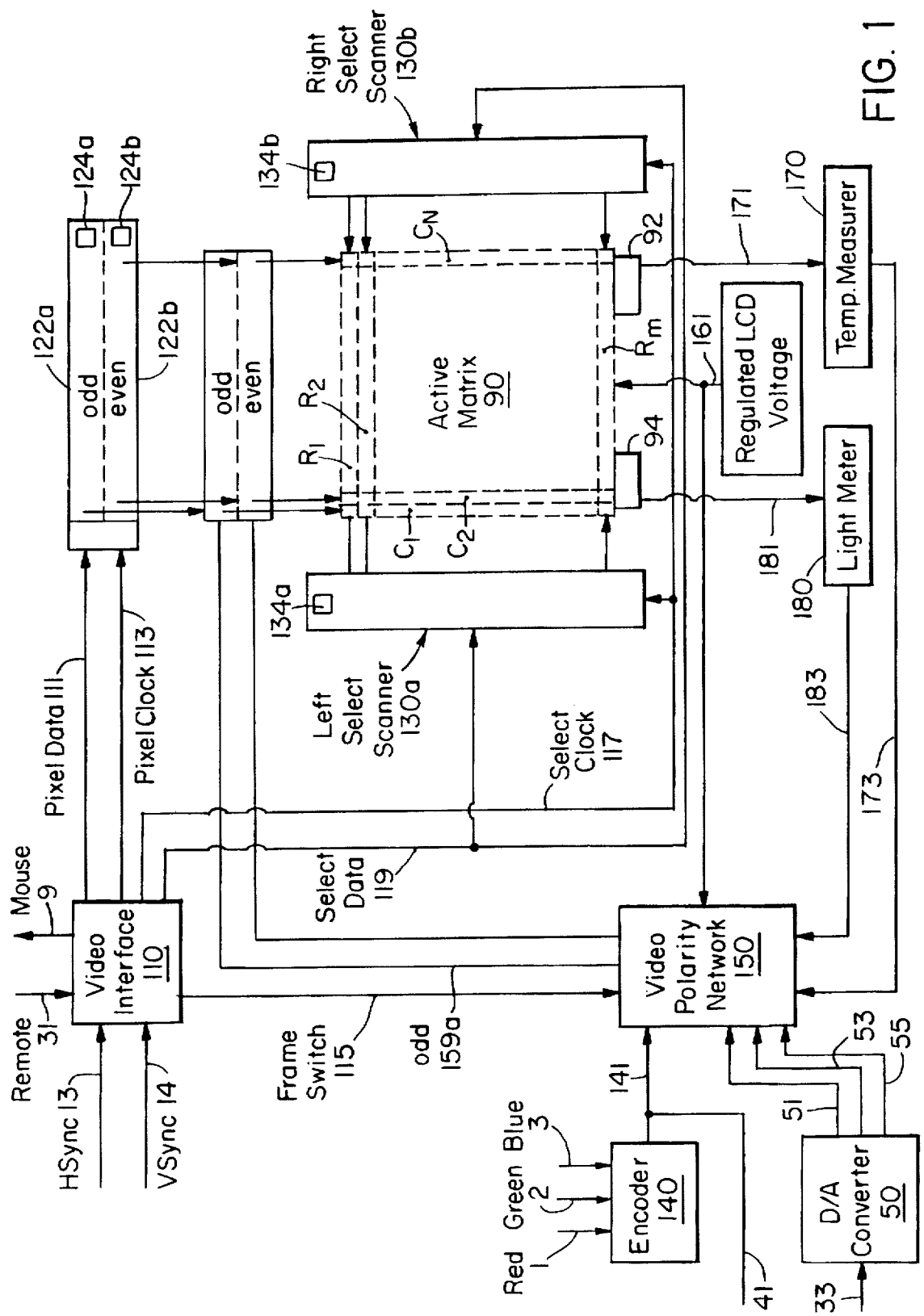
FIG. 1 is a schematic block diagram of a preferred embodiment of the invention.

A preferred embodiment is shown in FIG. 1. A video signal source (not shown) provides video signals to an active matrix display device (shown in phantom). The video signal source can be any analog or digital video signal source including a Video Graphics Array (VGA) adaptor, the Apple™ Macintosh™ family of computers, a National Television Systems Committee (NTSC) composite video source, a high-resolution professional display adapter, a Charge-Coupled-Device (CCD), or other similar sources. In a particular preferred embodiment, the active matrix display device is adapted as a computer-controlled light valve that substitutes for a positive photographic slide in a standard 35 mm slide projector. A detailed description of the particular preferred active matrix display device can be found in the patent application U.S. Ser. No. 08/106,071 by Matthew Zavracky et al., entitled "Slide Projector Mountable Light Valve Display," filed on Aug. 13, 1993, and incorporated herein by reference.

Horizontal and vertical synchronization signals from the video signal source are provided to a video interface 110 on data lines 13 and 14, respectively. Red-Green-Blue (RGB) video signal components, if supplied by the video signal source, are provided to an encoder 140 on respective data lines 1, 2, 3. If discrete color (e.g., RGB) signals are not supplied by the video source (e.g., NTSC composite video signal), then a single encoded video signal 41 must be supplied by the video source. The appropriate video signal is supplied to a video polarity network 150 on data line 141, the operation of which is described in greater detail below.

The active matrix 90 (shown in phantom) operates as a multi-frequency display device. Typically, video signals from the video signal source will not be synchronized to a fixed frequency. A change in the video mode can change the resolution of the data, measured in pixels. For example, a VGA adaptor generates synchronization signals that vary depending on the particular video mode in which the adaptor is operating. A standard VGA adaptor can generate a vertical synchronization frequency between about 56 and 70 Hz and a horizontal synchronization frequency between about 15 and 35 Khz. For professional display purposes (e.g., CAD/CAM) the vertical and horizontal synchronization frequency can be higher than described. To handle current high resolution display applications, the display device can preferably adapt to vertical synchronization frequencies up to about 100 Hz and horizontal synchronization frequencies up to about 66 Khz. In addition, a change in the video mode can also invert the polarities of the synchronization signals. Consequently, a preferred embodiment of the invention adapts to changes in the synchronization signals caused by changes in the video mode.

The video interface 110 is used to interface the active matrix display device with the horizontal and vertical synchronization signals from the video signal source. In a preferred embodiment, the video interface 110 interfaces with a standard VGA display adapter to display the video image at a horizontal resolution of 640 pixels and a vertical resolution of 480 pixels (640H×480V). In another preferred embodiment, the display resolution is 1024H×768V. In yet another preferred embodiment, the display resolution is 2048H×2048V. The video interface 110 adjusts to changes in the input synchronization frequencies by detecting polarity, frequency, or phase changes in the input signals.

A preferred embodiment of the invention for use with video signals for a VGA adaptor supports 720H×400V text mode, 640H×480V graphics mode, 640H×400V graphics mode and 640H×350V graphics mode. Table I summarizes video rates and resolutions associated with these supported VGA modes. It will be understood that other video modes having different video rates and resolutions can be supported as well, with minor modifications.

TABLE I

TYPICAL VGA RATES AND RESOLUTIONS

| Mode | Graphics | Graphics | Graphics | Text |
|---|---|---|---|---|
| Resolution | 640 H × 480 V | 640 H × 400 V | 640 H × 350 V | 720 H × 400 V |
| Pixel Rate | 25.175 MHz | 25.175 MHz | 25.175 MHz | 28.322 MHz |
| Horizontal Rate | 31.47 KHz | 31.47 KHZ | 31.47 KHz | 31.47 KHZ |
| Vertical Rate | 59.94 HZ | 70.08 Hz | 70.08 Hz | 70.08 Hz |
| Hsync Polarity | Negative | Negative | Positive | Negative |
| Vsync Polarity | Negative | Positive | Negative | Positive |

HORIZONTAL

| | Time | Pixels | Time | Pixels | Time | Pixels | Time | Pixels |
|---|---|---|---|---|---|---|---|---|
| Active Scan | 25.42 uS | 640 | 25.42 uS | 640 | 25.42 uS | 640 | 25.42 uS | 720 |
| Front Porch | 0.64 uS | 16 | 0.64 uS | 16 | 0.64 uS | 16 | 0.64 uS | 18 |
| Sync Width | 3.81 uS | 96 | 3.81 uS | 96 | 3.81 uS | 96 | 3.81 uS | 108 |
| Back Porch | 1.91 uS | 48 | 1.91 uS | 48 | 1.91 uS | 48 | 1.91 uS | 54 |
| Back Porch | 1.91 uS | 48 | 1.91 uS | 48 | 1.91 uS | 48 | 1.91 uS | 54 |

VERTICAL

| | Time | Lines | Time | Lines | Time | Lines | Time | Lines |
|---|---|---|---|---|---|---|---|---|
| Active Scan | 15.25 mS | 480 | 12.71 mS | 400 | 11.12 mS | 350 | 12.71 mS | 400 |
| Front Porch | 0.35 mS | 11 | 0.38 mS | 12 | 0.18 mS | 37 | 0.38 mS | 12 |
| Sync Width | 0.06 mS | 2 | 0.06 mS | 2 | 0.06 mS | 2 | 0.06 mS | 2 |
| Back Porch | 1.02 mS | 32 | 1.11 mS | 35 | 1.91 mS | 60 | 1.11 mS | 35 |
| Total Period | 16.68 mS | 525 | 14.27 mS | 449 | 14.27 mS | 449 | 14.27 mS | 449 |

Connection to a VGA adapter is through a traditional 15-pin, 3 row connector. The pin connections for the VGA receptacle are illustrated in FIG. 2A. Table II defines the pinouts for a typical VGA adapter. Table III lists the pinouts for the receptacle in FIG. 2A. Video signals are carried on pin 1, 2, 3, 5, 6, 7, 8, 10, 13 and 14. These pins are identical between the VGA connection and the control system connection. Pin 9 is used by a preferred embodiment of the invention as an EIA mouse out signal line. Pin 9 together with the equipment ground (pin 5) are provided to a mouse port on the receiving computer through an appropriate connector. In addition, pin 15 is used to receive a Mac detect signal to help detect Apple machines. FIG. 2B is a schematic diagram illustrating a VGA to video control system cable. Note that the computer end has two connections: a 15-pin, 3-row plug for the video information, and an appropriate plug for the mouse connector. To connect to a standard COM port, a 9-pin DSUB plug connector is used as the mouse connector.

TABLE II

VGA PINOUTS

| Pin | Function | Pin | Function | Pin | Function |
|---|---|---|---|---|---|
| 1 | Red | 6 | Red Return | 11 | ID0 |
| 2 | Green | 7 | Green Return | 12 | ID1 |
| 3 | Blue | 8 | Blue Return | 13 | Horiz Sync |
| 4 | ID2 | 9 | No Pin | 14 | Vert Sync |
| 5 | Equip Gnd | 10 | Sync Return | 15 | No Connect |

TABLE III

CONTROL SYSTEM PINOUTS

| Pin | Function | Pin | Function | Pin | Function |
|---|---|---|---|---|---|
| 1 | Red | 6 | Red Return | 11 | EIA In |
| 2 | Green | 7 | Green Return | 12 | ID1 |
| 3 | Blue | 8 | Blue Return | 13 | Horiz Sync |
| 4 | TTL ADB | 9 | EIA Mouse Out (PC) | 14 | Vert Sync |
| 5 | Equip Gnd | 10 | Sync Return | 15 | Mac Detect |

A preferred embodiment of the invention for use with Apple™ MAC-II computers, including the Powerbook™ series, supports 640H×480V resolution. In particular, the computer is informed that the active matrix display 90 is a 13-inch, 640H×480V Apple™ monitor. This does not imply that the same video timing is used on all Apple™ computers. If the correct timing cannot be determined, differences may manifest as centering offsets, which can be adjusted to zero. Table IV summarizes video rates and resolutions associated with an Apple™ MAC-II computer.

TABLE IV

TYPICAL MAC-II RATES AND RESOLUTIONS

| Monitor | 13 inch |
|---|---|
| Resolution | 640 × 480 |
| Pixel Rate | 30.24 MHz |
| Horizontal Rate | 35.00 KHZ |

TABLE IV-continued

TYPICAL MAC-II RATES AND RESOLUTIONS

| Vertical Rate | 66.67 HZ |
| CSync Polarity | Negative |

HORIZONTAL

|  | Time | Pixels |
| --- | --- | --- |
| Active Scan | 21.16 uS | 640 |
| Front Porch | 2.12 uS | 64 |
| Sync Width | 2.12 uS | 64 |
| Back Porch | 3.18 uS | 96 |
| Total Period | 28.57 uS | 864 |

VERTICAL

|  | Time | Lines |
| --- | --- | --- |
| Active Scan | 13.71 Ms | 480 |
| Front Porch | 0.09 Ms | 3 |
| Sync Width | 0.09 mS | 3 |
| Back Porch | 1.11 mS | 39 |
| Total Period | 15.00 mS | 525 |

Figure 2D:
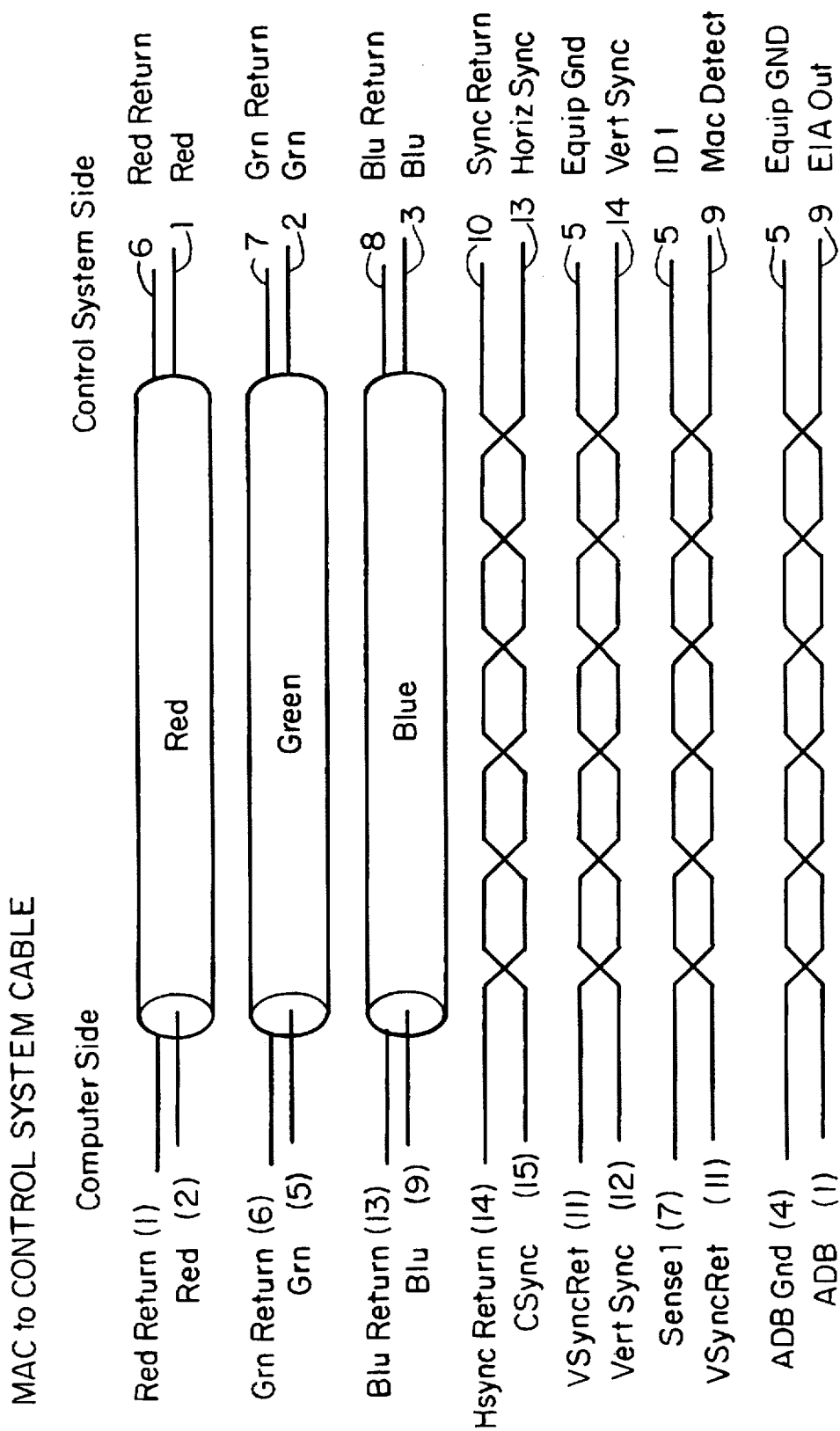

Connection to an Apple MAC-II computer is through a 15-pin, 2 row connector. The Macintosh video connector is illustrated in FIG. 2C. The Macintosh video pinout definitions are provided in Table V. The video control system pin definitions are the same as defined in Table III. FIG. 2D is a schematic diagram illustrating a Macintosh computer to video control system cable.

TABLE V

MAC PINOUTS

| Pin Function | Pin Function | Pin Function |
| --- | --- | --- |
| 1 Red Return | 6 Green Return | 11 VSync/CSync Return |
| 2 Red | 7 Sense 1 | 12 Vert Sync |
| 3 Composite Sync | 8 No Connect | 13 Blue Return |
| 4 Sense 0 | 9 Blue | 14 Horiz Sync Return |
| 5 Green | 10 Sense 2 | 15 Horiz Sync |

Preferably, a preferred embodiment of the invention also supports the Apple™ MAC-LC video family. The MAC-LC computer can generate signals to drive either a 13-inch 640H×480V Apple™ monitor or a VGA monitor, using a special monitor adaptor available from Apple Computer, Inc. When connected directly to the MAC-LC computer, the video control system functions as a 13-inch 640H×480V Apple™ monitor. When the monitor adaptor is installed, the video control system receives quasi-VGA signals. The video control system detects the actual video mode sent by the computer. Unfortunately, the timing of the Apple™ quasi-VGA signal is not identical to the VGA specification. This timing difference results in the horizontal centering being four pixels off, which can be adjusted using centering controls. Table VII summarizes video rates and resolutions associated with an Apple™ MAC-LC product.

TABLE VI

TYPICAL MAC-LC RATES AND RESOLUTIONS

| Monitor | 13 inch | VGA |
| --- | --- | --- |
| Resolution | 640 H × 480 V | 640 H × 480 V |
| Pixel Rate | 31.3344 MHZ | 25.175 MHz |
| Horizontal Rate | 34.97 KHz | 31.47 KHz |

TABLE VI-continued

TYPICAL MAC-LC RATES AND RESOLUTIONS

| Vertical Rate | 66.61 Hz | 59.94 HZ |
| Hsync Polarity | Negative | Negative |
| Vsync Polarity | Negative | Negative |

HORIZONTAL

|  | Time | Pixels | Time | Pixels |
| --- | --- | --- | --- | --- |
| Active Scan | 20.43 uS | 640 | 25.42 uS | 640 |
| Front Porch | 2.55 uS | 80 | 0.48 uS | 12 |
| Sync Width | 2.04 uS | 64 | 3.81 uS | 96 |
| Back Porch | 3.57 uS | 112 | 2.07 uS | 52 |
| Total Period | 28.59 uS | 896 | 31.78 uS | 800 |

VERTICAL

|  | Time | Lines | Time | Lines |
| --- | --- | --- | --- | --- |
| Active Scan | 13.73 mS | 480 | 15.25 mS | 480 |
| Front Porch | 0.09 mS | 3 | 0.32 mS | 10 |
| Sync Width | 0.09 mS | 3 | 0.06 mS | 2 |
| Back Porch | 1.11 mS | 39 | 1.05 mS | 33 |
| Total Period | 15.01 mS | 525 | 16.68 mS | 525 |

Video signal from the appropriate video connector are fed to the video control system. FIGS. 3A–3C are block diagrams of a preferred video interface 110 for VGA signals.

Referring to FIG. 3A, horizontal and vertical synchronization signals are provided at TTL levels on respective incoming data lines 13, 14 from a VGA adapter or similar video source. A control processor 112 examines the incoming video stream and tracks mode changes, which provide for variable frequency multi-scanning capability. Upon detecting a mode change, the control processor 112 signals the mode change to a dot clock regenerator 114 over data line 116. Optionally, the control processor 112 interprets input signals from a remote control device over a remote signal line 31 and either controls hardware or provides remote mouse functionality over a mouse signal line 9 to the computer, as required. Preferably, a non-volatile Editable Erasable Programmable Read-Only Memory (EEPROM) is used to store setup and adjustment parameters. The program for the processor is contained within a Erasable Programmable Read-Only Memory (EPROM) which simplifies upgrading the functionality of the program. Most digital logic is contained within Field Programmable Gate Arrays (FPGAs), which are also programmed from the same EPROM. Upgrading the EPROM allows functionality to be changed, added or repaired, all with little manufacturing cost. The dot clock regenerator 114 provides a pixel data signal on line 111, a pixel clock signal on line 113, a frame switch signal on line 115, a select clock signal on line 117, and a select data signal on line 119.

As illustrated in FIG. 3B, the dot clock regenerator 114 recreates the pixel dot clock used by a computer to output pixels. The regeneration must be accurately controlled because it is very important to provide a clock that is centered over each pixel and does not drift. Thus, a clock must be recreated that can be used to sample a pixel and move to the next pixel. The dot clock regenerator 114 includes a phase locked loop (PLL) network 114a and Voltage Controlled Oscillator (VCO) 114b. The PLL 114a and VCO 114b are responsive to the mode change signal over data line 116. There is no standard for the frequency of the incoming video signal, which can range from 20 Mhz to over 30 Mhz, depending on the source.

An analog RGB signal is not quantized because CRTs do not require the analog signal to have a notion of screen position. Unlike CRTs, flat panel displays have quantized pixels. Hence, the analog RGB signal must be quantized to each pixel. For the quantization to be accurate, each scan line of the analog RGB signal must be divided into discrete values. That task is performed by the dot clock regenerator 114. As summarized in Table I, the VGA 640H×480V modes include 800 pixels per horizontal scan. Unfortunately, only one timing signal (i.e., the horizontal sync) is received per scan line. Thus, the PLL 114a must operate with a divider multiplication ratio of 800:1. Typical phase-lock loop circuits become unstable at divider multiplication ratios over about 8:1. PixelVision, Inc. of Acton, Mass. manufactures and sells video processing circuitry containing a preferred dot clock regenerator 114, under Part Nos. PV-CIFK-xxxx. Other suitable dot clock regenerators 114 may be available from other sources. The dot clock regenerator 114 preferably permits a user to fine tune the position of the reconstructed dot clock, through the control processor 112.

Although the active matrix 90 is an analog device, video signals must be "massaged" before being presented to the active matrix 90. In general, the video signal is to be presented to the active matrix 90 through two inputs, each a mirror of the other. Both signals are to be biased on a nine-volt reference, with the video having a six volt, peak-to-peak swing. At least 50 Mhz bandwidth must be maintained, into a 100 pf load. The voltages and currents required in this particular embodiment are detailed in Table VII.

TABLE VII

| Center Voltage (volts) | Range (volts) | Drive (milliamps) |
|---|---|---|
| +3 | 2.5 to 4.5 | 70 (Sink) |
| +9 | 7 to 11 | +/−2 |
| +15 | 11.5 to 16 | 75 (Source) |

FIG. 3C is a schematic block diagram of the logic drive 160 for the active matrix 90. Overall, the logic drive 160 receives common logic level inputs, preferably CMOS or TTL and translates them to the drive levels required by the active matrix 90.

A tracking regulator 166 provides a DC voltage approximately two volts higher than the panel voltage supply to the active matrix 90. The panel voltage itself is adjustable, to allow operation with different liquid crystal types. The tracking regulator 166 is a small linear regulator, with an emitter follower output to supply the needed current.

A horizontal logic drive 163 provides the synchronizing pulse (i.e., pixel data 111) and clock (i.e., pixel clock 113) for the horizontal axis of the active matrix 90. This is the fast axis, where the video data is clocked into the display. A MOSFET driver is used, to provide the needed fifteen-volt logic swing into the 30 pF load at speeds commensurate with a maximum pixel rate (e.g., 31.5 Mhz). The clock is half the pixel rate, with each edge being used to enter pixels. Another reason for the output voltages to quickly reach near the panel voltage, or ground, is to limit power dissipation in the active matrix circuitry. This is especially important for the clock, because the edge rate is high. Another reason for fast edge rates is sampling jitter; slow edges lead to timing uncertainty. To increase the positive-going edge rate, the voltage from the tracking regulator 166 is used to provide some overdrive. In the negative-going direction there is already overdrive, because the negative panel supply is a nominal three volts.

With the overdrive from the driver, there would be some danger of overloading the input clamp to the active matrix 90. This is prevented by, first, including a small current limiting resistor 167a, 167b in series with each output. There is also a diode clamp 168a, 168b to the panel voltage. The current limiting resistor 167 together with the diode clamp 168 prevents the input clamp to the active matrix 90 from being overly stressed.

A vertical logic drive 162 provides the synchronizing pulse (i.e., select data 119) and clock(s) (i.e., select clock 117) for the vertical axis of the active matrix 90. This is the slow axis, where a clocking edge occurs every scanline. A MOSFET driver is used here, as with the horizontal axis, except without overdrive.

Returning to FIG. 1, the video interface 110 converts the synchronization signals from the video signal source into pixel timing information for the pixel columns and select line timing information for the pixel rows of the active matrix. The video interface 110 provides control registers to adjust and delay the pixel clock 113, pixel data 111, select clock 117, and select data 119 so the image generated by the video source (e.g. VGA) can be precisely mapped to the active matrix 90 pixel resolution (e.g., 640H×480V). The video interface 110 provides a pixel data signal and a pixel clock signal to a data scanner 120 on respective data lines 111,113. The video interface 110 also provides a select line data signal and a select line clock signal to select scanners 132,136 on respective data lines 117,119. Preferred embodiments of the invention supply one or four clocks on each clock signal line 113,117. By supplying four clock signals on each clock signal line 113,117, the circuitry of the scanners 120,130 can be simplified. This is especially important if the scanners 120,130 are fabricated on the SOI structure with the active matrix 90 and the video interface 110 is a discrete component. Finally, the video interface 110 provides a frame switch signal to the video polarity network 150 on data line 115.

Encoder 140 may be a gray-scale encoder or a color encoder. The RGB signal is provided from the pinout connectors on signal lines 1,2,3. The encoder converts the RGB signal into a mapped analog signal. A gray-scale encoder employs a colored mapper to convert the RGB signal into a gray-scale equivalent. In a preferred embodiment, each color from the RGB signal is weighted and then summed together to form a gray-scale signal. The gray-scale mapper uses the equation $$V_o = W_R V_R + W_G V_G + W_B V_B, \qquad (1)$$

where $V_o$ is the gray-scale output signal; $W_R$, $W_G$, and $W_B$ are the respective weighting for the red, green and blue signals; and $V_R$, $V_G$, and $V_B$ are the respective signal strengths for the red, green and blue signals. In a preferred embodiment of the invention, $W_R=0.3$, $W_G=0.59$ and $W_B=0.11$ to result in a weighting function approximately equal to the human eye's relative response. However, other weighting values can be obtained by changing resistor values in the circuit. If the video source supplies a monochrome signal, that signal is preferably applied at the green input 2. In addition, other mapping techniques may be employed without affecting the scope of the invention (e.g., digital mapping). A color encoder employs a multiplexer to multiplex the RGB signal into a mixed color equivalent. In a preferred embodiment, the encoder 140 provides either one of gray-scale or color encoding, as required. The encoded analog signal from either the gray-scale mapper or color encoder is provided to the video polarity network 150 via an encoder line 141.

In a further embodiment, the video source can provide an NTSC composite video signal on signal line 123. In an NTSC composite video signal, the RGB signals and the synchronization signals are superposed as a single analog video signal. Because the RGB signals are already encoded in a NTSC composite video signal, no separate encoding is necessary. Instead, the superposed RGB data is extracted from the NTSC composite video signal. The superposed RGB data from an NTSC composite video source is provided to the video polarity network 150 on line 141.

Figure 4:
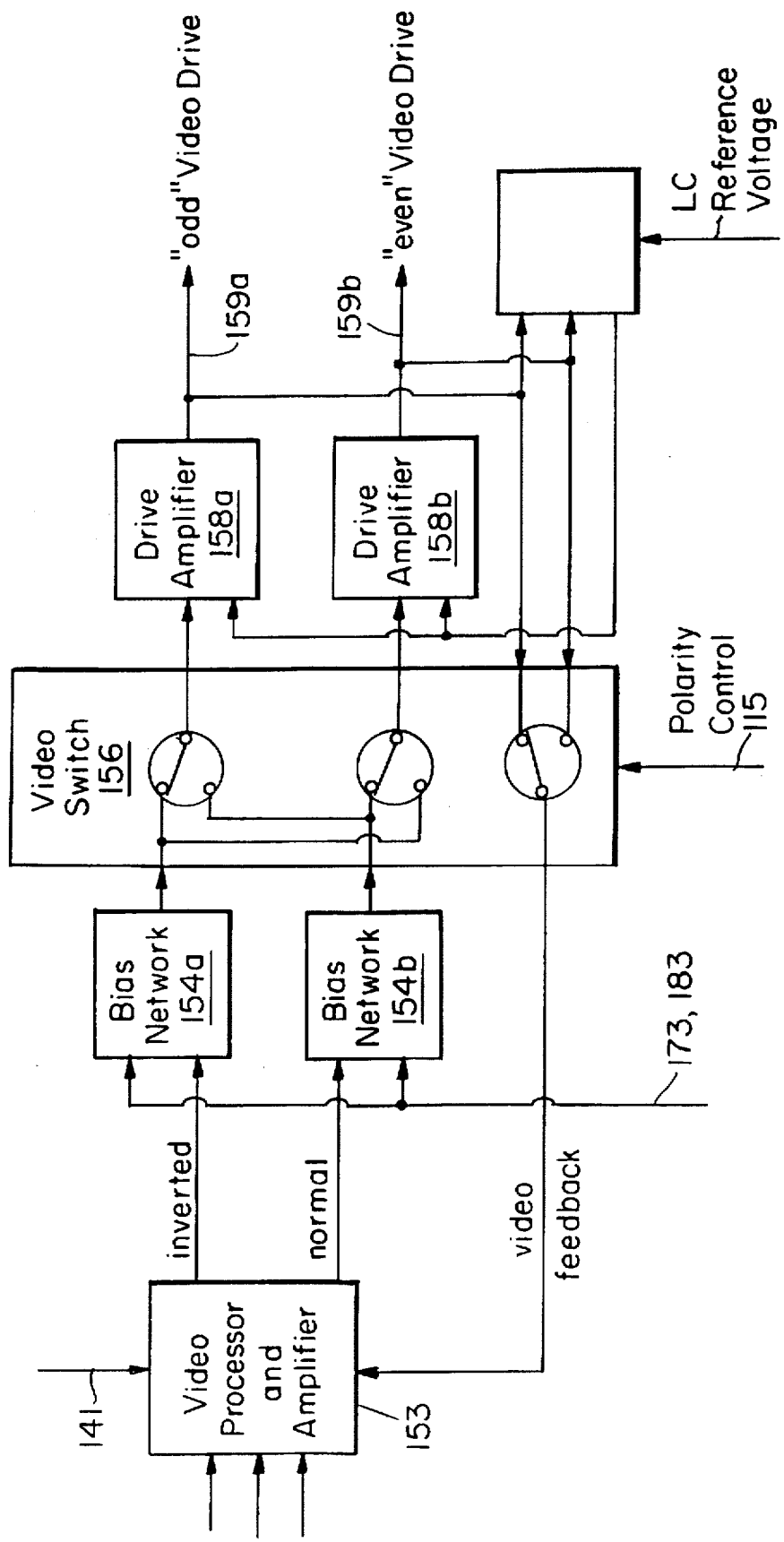
FIG. 4 is a schematic block diagram of a preferred video polarity network 150 of FIG. 1.

The video polarity network 150 generates odd and even video driven signals 159 from the frame switch data on line 115 and the analog video signal on line 141. The video drive signal 159 is adjusted by a contrast control signal 51, a back porch clamp signal 53, a brightness control signal 55, the liquid crystal reference voltage 161, and feedback signals 173, 183 from a temperature measurer 170 or light meter 180. As shown in FIG. 4, the video polarity network 150 incorporates a video amplifier 152, bias network 154, a video switch 156, drive amplifiers 158 and a DC level control servo 155.

The analog video signal from line 141 is provided to the video amplifier 152. The video input 141 is amplified by an amount determined by the contrast (gain) control voltage 51 generated by a digital-to-analog (D/A) converter 50. Because the video input is AC coupled, the DC restore function is done by a back porch clamp (not shown). The Brightness (level) control 55 is the reference voltage for the clamp which is obtained from the D/A converter 50. The feedback for the clamp is taken from the main video outputs, which closes the loop around the full video path. In a preferred embodiment, this block is implemented by a National Semiconductor LM1201 amplifier, although other suitable amplifiers can be used.

One important feature is that there are two complementary outputs from the video amplifier 152. The normal output 153b is positive-white from a (clamped) level a few volts above ground. The inverted output 153a is negative white from a few volts below the positive supply voltage (12V). These two outputs 153a, 153b are inherently in phase, and have the same gain because they are preferably taken from the same output transistor. Alternatively, the amplifier gain can be nonlinear (e.g., gamma functions). The normal and inverted amplifier signals 153a, 153b are fed to a bias network 154.

The bias network 154 is an RC network that biases the two outputs of the video amplified 152 toward each other. Those outputs can never reach the same voltage, due to the nature of the output stage. But the inputs to the drive amplifiers 158 should be capable of crossing over in some cases, to allow a full range of contrast and brightness adjustment. The output signals from the bias network 154 are fed to the video polarity switch 156.

To provide the AC component of the required active matrix drive signal, video switches select either the normal or the inverted video signals. These video signals are supplied alternately to an odd drive amplifier 158a, with an even drive amplifier 158b receiving the opposite signal. Preferably, the switches change every video field (every vertical sync). The switch could occur more or less often, as might be desirable for crosstalk or other purposes; a preferred switching rate allows switching every scanline. The switches used are FET-based "T" switches, which provide good isolation and fairly low "on" resistance. A switch is also used to select between the outputs, to always provide a "normal" feedback signal for clamping comparison. The video polarity switch 156 is synchronized to the frame rate provided over the frame switch line 115.

In a preferred embodiment, a column inversion technique is used to reduce crosstalk between select lines to reduce or avoid the production of a DC offset voltage. The video switch 156 provides an alternating opposite polarity for the column pixels. The even column pixels are operated at the opposite polarity of the odd column pixels. The polarities of the column pixels are switched on each sequential frame. For example, on one frame even column pixels operate at a positive polarity and odd column pixels operate at a negative polarity. On the next sequential frame, the switch 156 switches the polarities of the odd and even columns. As a result, the even column pixels operate at a negative polarity and the odd column pixels operate at a positive polarity. The odd column polarity is provided to the active matrix on line 159b and the even column polarity is provided to the active matrix on line 159a.

Another preferred embodiment of the invention uses a frame inversion technique instead of column inversion. Using frame inversion, each column during any one frame has the same polarity. On alternating frames, as clocked by the frame switch 115, the polarity of each column is reversed. In that way, the polarity of the entire active matrix 90 is inverted on each successive frame. Note that this frame inversion embodiment would not require the use of distinct odd and even data registers 122.

The video drive to the active matrix 90 is preferably implemented with current feedback operational amplifiers 158. These amplifiers 158 can drive the high load capacitance while remaining stable and retaining adequate frequency response. Two amplifiers 158a,158b are provided, for the odd and even pixel inputs of the active matrix 90. Both inputs receive the full video signal, with correct pixel data selected by the clock inputs discussed above. The operational amplifiers 158 are used in a non-inverting configuration, with the feedback networks referenced to the output of the DC-level control servo 155. There is a small output resistor, to limit peaking and overshoot. Alternatively, an RC snubber can be coupled to ground. The nominal gain of this stage is preferably 2.3.

The DC level control servo 155 adjusts the operating level of the drive amplifiers 158 so there is a minimal overall DC voltage applied across the liquid crystal material. A significant DC voltage could damage the liquid crystal material. A regulated LCD voltage 161 is supplied to the servo 155 as a center reference voltage of the liquid crystal material. The servo 155 filters the two video outputs 159, to establish their average level. The difference between this average and the reference voltage is integrated, with the result providing a feedback voltage for the drive amplifiers 158. Thus, the loop is closed, and drives to "zero" error. The integrator output stage has a discrete emitter follower to handle the current required by the drive amplifiers 158. With fixed 1% resistors, the residual error should be less than 100 mV. With a potentiometer as well, as used in a preferred embodiment, the DC level error can be further adjusted as needed.

The data scanner 120 provides for double storage of pixel data. The data scanner 120 interfaces with the pixel data signal on line 111 and the pixel clock signal on line 113 via interface component 125. The data scanner 120 uses an odd shift register array 122a and an even shift register array 122b to store data for each scan. The odd shift register array 122a stores data to odd column pixels and the even shift register array 122b stores data to even column pixels. To facilitate fabrication testing, an odd test pad 124a is fabricated on the odd shift register array 122a and an even test pad 124b is fabricated on the even shift register array 122b.

A transmission gate 126 transmits pixel actuation signals to the active matrix 90. The transmission gate 126 is partitioned into odd column gate 128a and even column gate 128b, which are registered to respective columns of the data scanner shift registers 122a,122b. A serial data stream of a video drive signal is provided to the odd and even column pixels on respective signal lines 159a,159b. An appropriate signal level is transmitted by the transmission gate 126 to the correct pixel as triggered by the output from the shift registers 122.

To reduce signal loss across the active matrix, the select lines are driven from both sides by select scanners 130. As viewed in FIG. 1, left select scanner 130a and right select scanner 130b are connected to the select data line 119 and the select clock line 117. The left select scanner 130a provides a select line signal at the end of the select line nearest the lowest-valued pixel column ($C_l$) and right select scanner 130b provides a select line signal at the end of the select line nearest the highest-valued pixel column ($C_N$). Thus, an identical select line signal is supplied at both ends of the select line. To facilitate fabrication testing, a left scanner test pad 134a is fabricated on the left select scanner 130a and a right scanner test pad 134b is fabricated on the right select scanner 130b.

The shift registers of the data scanner 120 and the select scanners 130 are dynamic shift registers. The dynamic shift registers rely on capacitor storage without leakage. However, dynamic shift registers are susceptible to leakage, especially when they are exposed to light. Hence, light shields are needed to protect the scanners 120,130 from exposure to light.

In a further preferred embodiment, at least one sensor 92, 94 is integrated into the active matrix 90 for gray-scale adjustments. The sensor may be a temperature diode, a photo transistor or diode, or combinations thereof. Returning to FIG. 1, a preferred embodiment employs at least one temperature sensor 92 and at least one light sensor 94. The signals from the sensors provide feedback signals, to the video polarity network 150. In response to the feedback signal, the video amplifier 152 adjusts the gray-scale signal strength.

In a preferred embodiment, the sensors 92,94 are uniformly distributed throughout the active matrix. For example, each pixel element, or a selected group of pixel elements can have an associated sensor 92,94. The sensor to pixel ratio need not be one-to-one however. In another material embodiment, the sensors 92,94 are distributed around the perimeter of the active matrix.

Figure 5:
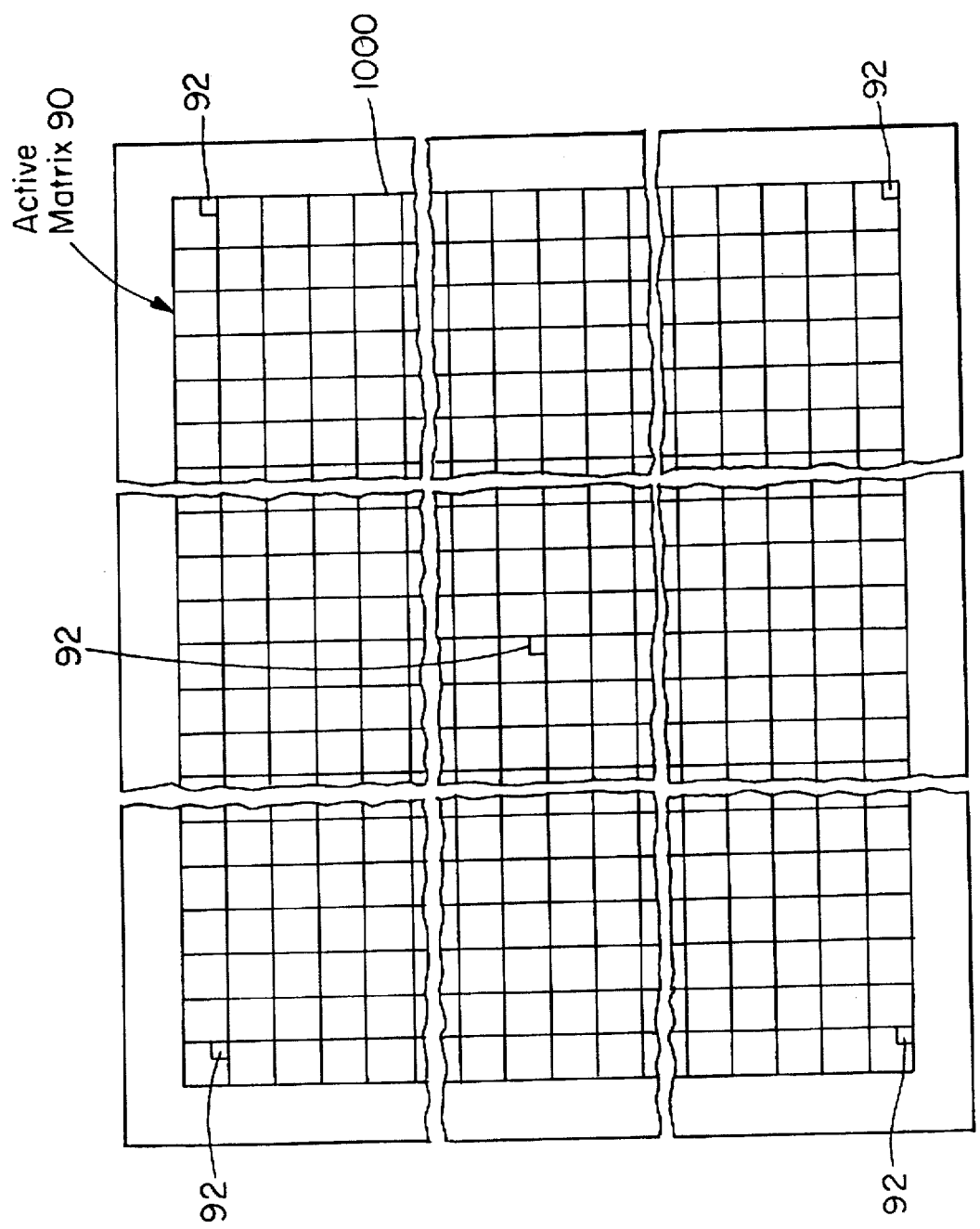
FIG. 5 is a view of the display device showing a preferred temperature sensor arrangement.

FIG. 5 shows a preferred temperature sensor arrangement. The active matrix 90 comprises a plurality of pixels 1000 arranged in columns and rows. Ideally, heat will be absorbed substantially uniformly throughout the liquid crystal material. Thus, only one temperature sensor 92 is necessary to measure the temperature of the active matrix 90. However, there will be local temperature variations due to the nature of the image being displayed. In addition, a plurality of temperature sensors can be used to provide redundancy. In the figure, temperature sensors 92 are distributed throughout the active matrix region 90. As shown, temperature sensors 92 are distributed around the perimeter of the active matrix 90. In particular, the temperature sensors 92 are located at corner pixels 1000 of the active matrix 90. In addition, a temperature sensor 92 is disposed near the center of the active matrix 90. Of course, more or less temperature sensors 90 may be used.

FIG. 6A shows a preferred light sensor arrangement. Light sensors are used to construct a transmittance curve for the liquid crystal material. The light sensors 94 are distributed around the active matrix region 94. In addition, there are sensors 941 to indicate a permanently dark pixel reading.

There are also sensors 942 that represent permanently white pixel readings. The permanent readings are provided by either connecting the sensors 94 to either a DC supply voltage or to ground. The permanent-valued sensors 941,942 map the end points of the liquid crystal material's transmittance curve. The light sensor 94 measures the transmission of light through the liquid crystal material in real time. The transmittance of the liquid crystal material varies with the temperature of the material.

Because all light between the polarizes 1095,1089 is polarized, a light sensor 94 located within the active matrix 90 cannot measure changes in the transmission of light through the liquid crystal material. To measure changes in the intensity of light, the light transmitted through the liquid crystal material 1081 must be measured after exiting the second polarizer 1089. Although a light sensor may be mounted outside the second polarizer 1089, a preferred embodiment of the invention fabricates the light sensor 94 as part of the SOI circuit 1058.

Figure 6B:
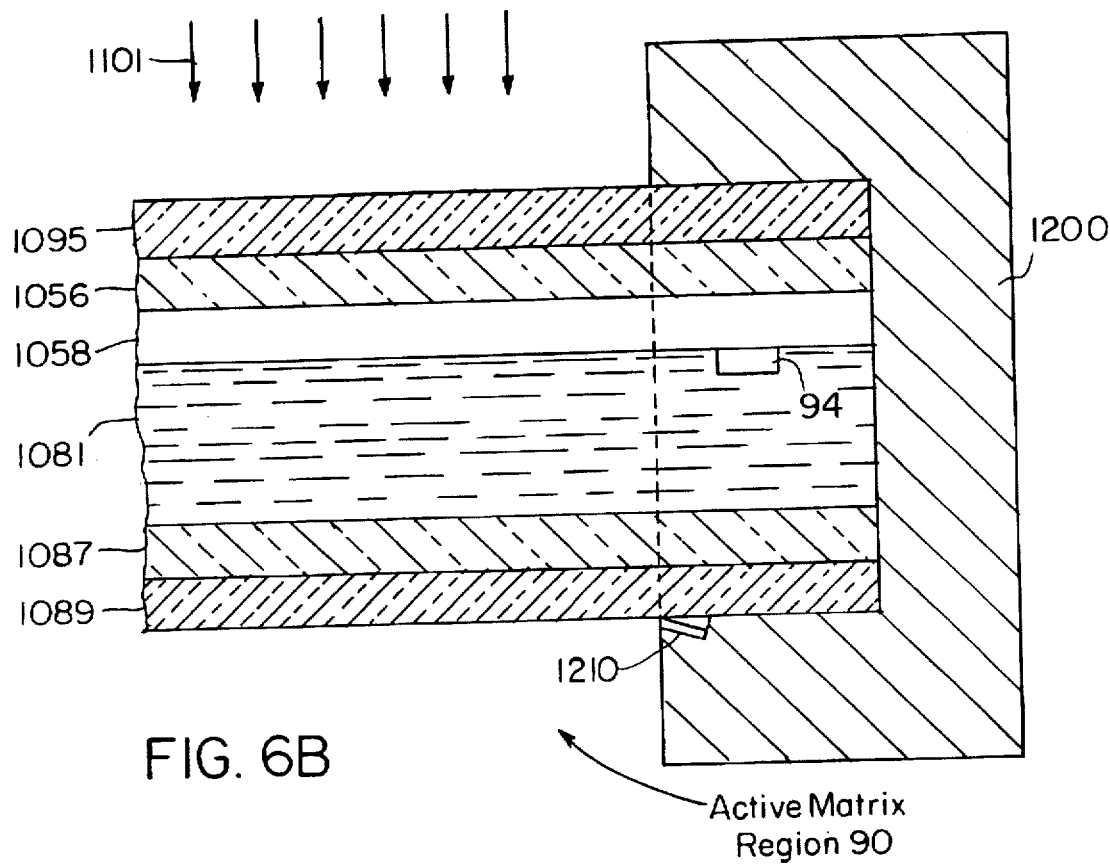
Figure 6C:
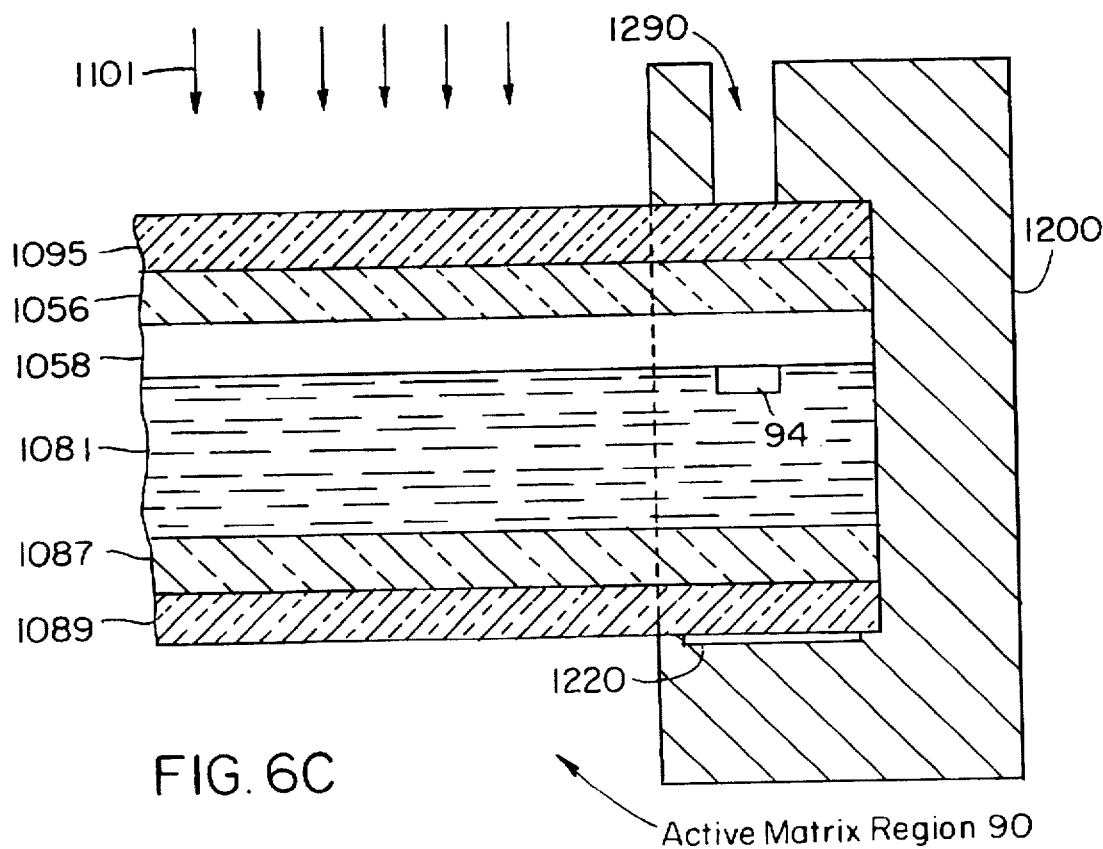

FIG. 6B–6C are partial cross-sectional views of the display area having a light sensor 94. In both figures, the light sensor 94 is located outside of the active matrix region 90. A preferred embodiment is shown in FIG. 6B. A reflector 1210 is mounted on a mechanical frame 1200. The reflector 1210 is inclined such that light that has passed through the liquid crystal material 1081 is reflected toward the light sensor 94. Light sensor 94 only measures relative change in light transmission. Therefore, only a minute quantity of light, such as collateral light, needs to be reflected toward the sensor 94.

An alternative embodiment is shown in FIG. 6C, where an aperture 1290 is provided through the mechanical frame 1200. The incident light 1101 enters the structure through the aperture 1290 and passes through the liquid crystal material. After passing through the liquid crystal material, the light 1101 is reflected by a reflector 1220 mounted on the mechanical frame 1220. The reflected light is thus reflected back to the light sensor 94, where the light intensity is measured. Although the light does not pass through the active matrix region 90, the transmittance can be calculated because the temperature of the liquid crystal material is essentially constant throughout. Therefore, the measurement by light sensor 94 is sufficiently accurate to determine the liquid crystal's relative position on the transmittance curve.

Figure 7A:
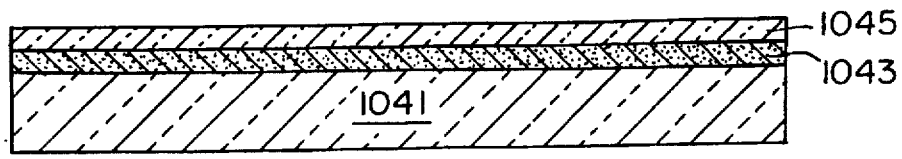
FIGS. 7a–7h illustrate a preferred processed flow sequence illustrating the fabrication of a transmissive active matrix display with a sensor.

FIGS. 7A–7H illustrates a preferred fabrication process for fabricating the sensors 92,94 into the active matrix. Referring to FIG. 7A, an SOI structure includes a silicon substrate 1041 and an insulating oxide layer 1043 (such as, for example, one micron of $SiO_2$) that is grown or deposited on the substrate 1041. A thin (i.e. 0.3 micron) single crystal layer 1045 of silicon is formed over the oxide 1043. The oxide is thus buried beneath the silicon surface layer, such that higher speed devices can be fabricated. However, it is noted that any number of techniques can be employed to provide a thin film of single crystal silicon.

Figure 7B:
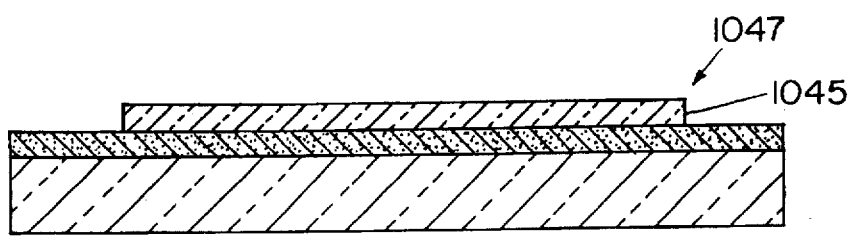
Figure 7C:
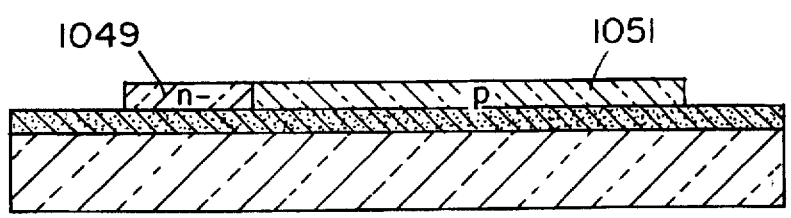

As shown in FIG. 7B, the film 1045 is patterned into islands to define each pixel elements 1047. As explained below, the pixel elements are then processed to form a transistor, an electrode, and sensors 92,94. To that end, the pixel elements are masked (not shown) and subjected to deep and shallow implants to form an n-well region 1049 (FIG. 7C). Another masked is formed over the pixel elements, and the elements are subjected to deep and shallow implants to form an p-well region 1051.

Figure 7D:
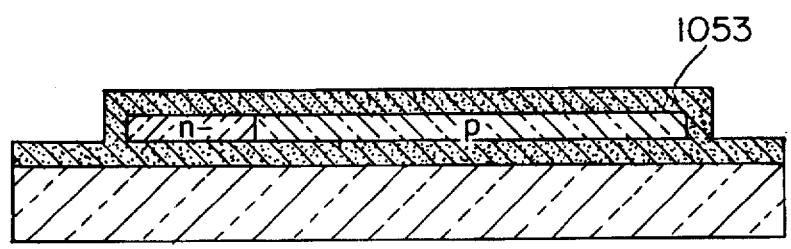
Figure 7E:
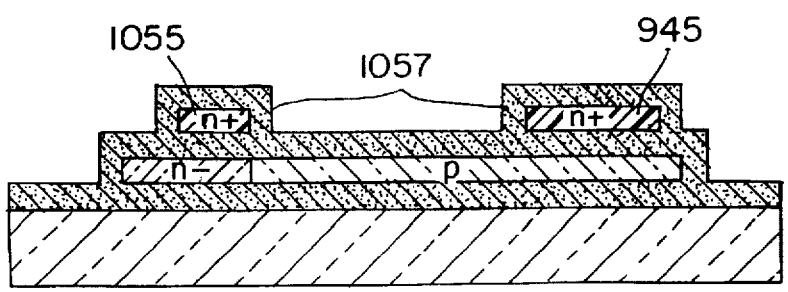

Referring to FIG. 7D, an $SiO_2$ layer 1053 having a thickness on the order of 0.07 micron is formed over each silicon island 1047. A layer of polysilicon having a thickness of about 0.5 micron is formed on the oxide layer 1053, doped to provide an n+ region and patterned to form a transistor gate 1055 and a diode junction 945 (FIG. 7E). Another oxide layer 1057 having a thickness of about 0.07 micron is formed over the polysilicon.

Figure 7F:
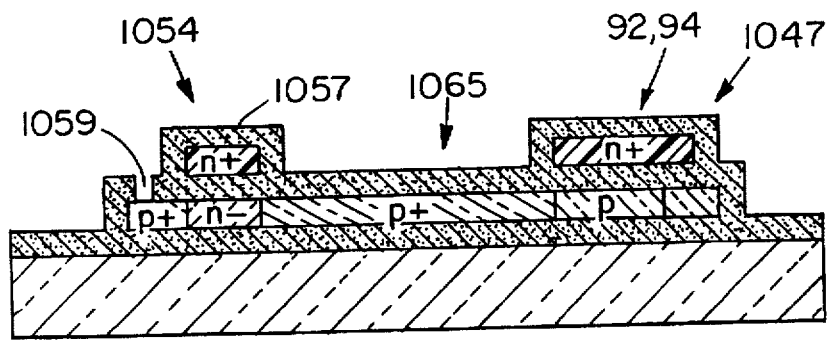

The pixel elements 1047 are masked (not shown) and doped with $2*10^{15}$ of phosphorous to provide an n+ source/drain implantation (FIG. 7F). After the mask is removed, the pixel elements are again masked and doped with $4*10^{15}$ of boron to provide a p+ source/drain implantation. As such, a transistor 1054, a pixel electrode 1065, and a sensor 92, 94 have been formed for pixel element 1047.

Figure 7G:
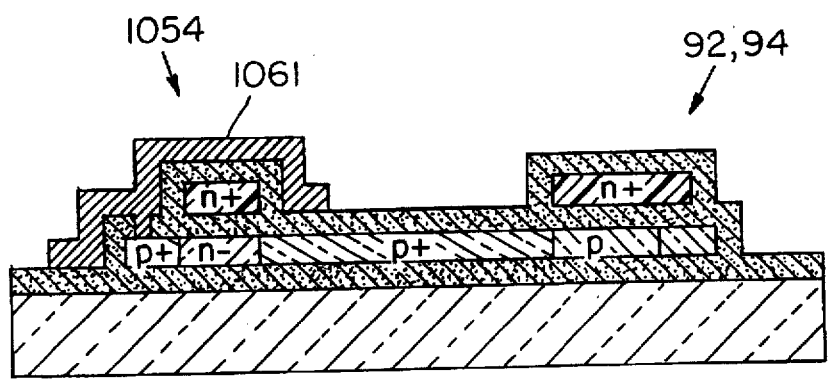

A portion 1059 of the oxide layer is then removed to form a contact for the transistor 1054. Referring to FIG. 7G, a metallization deposition is then performed to form a layer 1061 over the transistor 1054. The layer can comprise aluminum and has a thickness of about one micron. The layer 1061 serves as a pixel light shield as well as a contact for the transistor 1054.

Figure 7H:
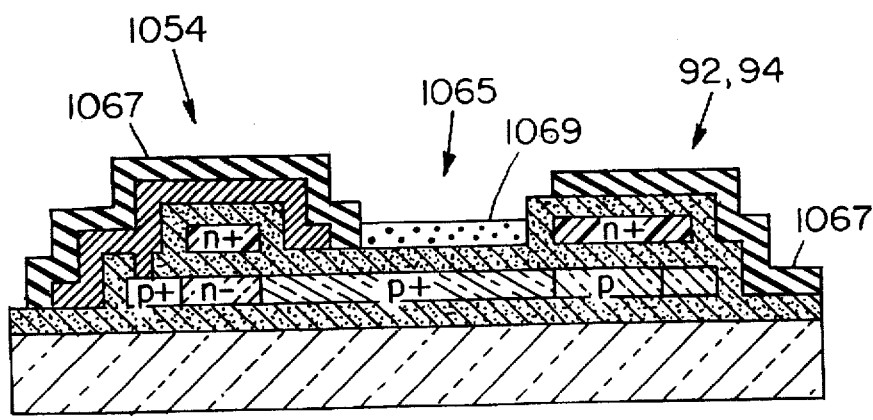

Referring to FIG. 7H, the entire pixel can be coated with a thin (about 0.15 micron) layer of silicon nitride (not shown). Next, a layer of amorphous silicon having a thickness of about 0.5 micron is deposited over each pixel element. The layer is then patterned to provide a matrix of black elements 1067, each black element associated with a transistor. A color filter element 1069 may be formed over the pixel electrode 1065. The color filter elements can be formed by processing an emulsion or a photoresist carrier, or by processing conventional filter materials. The individual color filter elements can be processed to provide an arrangement of three or four different color pixel elements in any of the previously described geometries.

Figure 8:
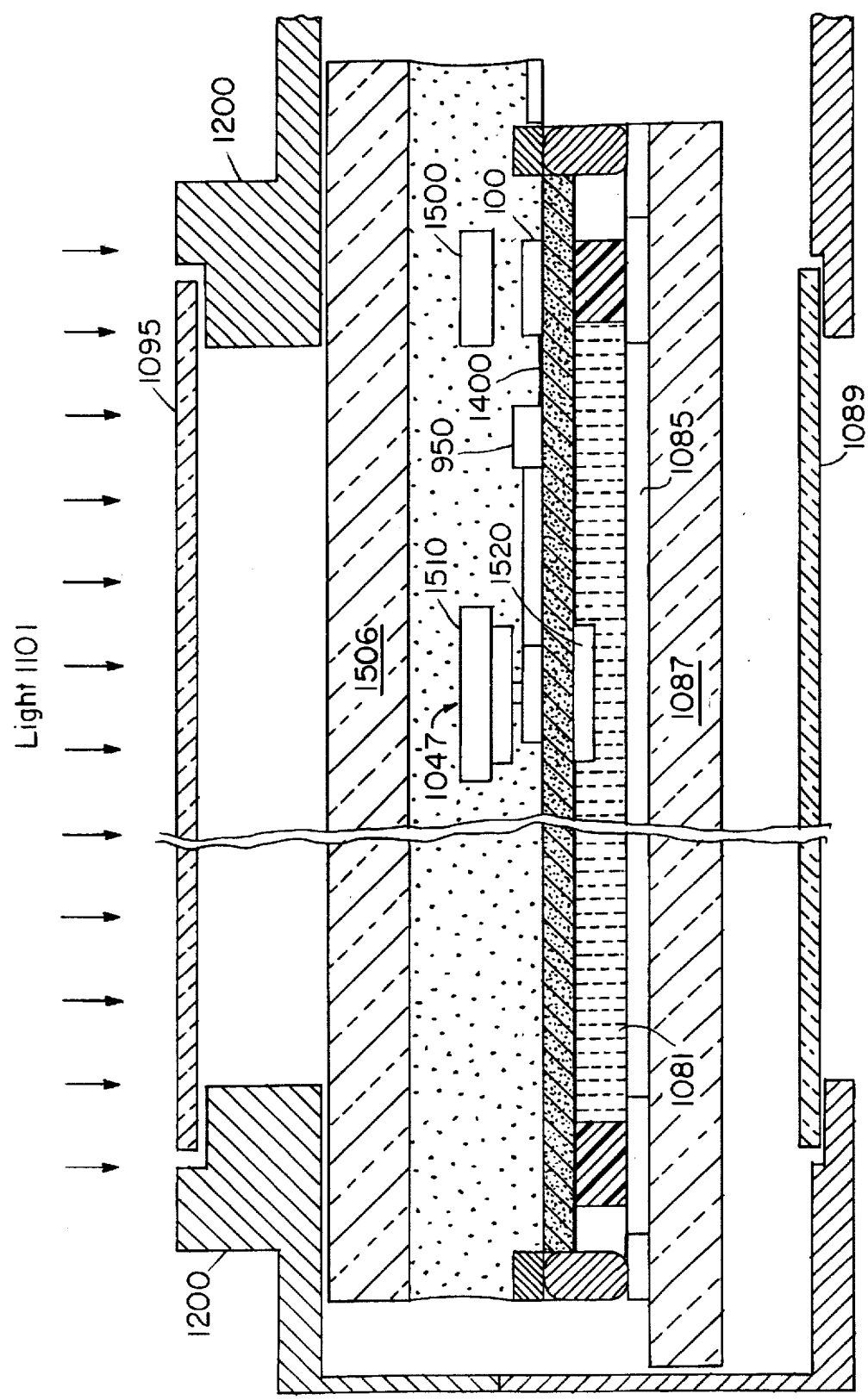
FIG. 8 is a partial cross-sectional view of a preferred active matrix display device.

FIG. 8 shows a partial cross sectional view of a preferred active matrix display device. The display device comprises polarizers 1089,1095, cover glass 1087, glass substrate 1056, counter electrode 1085, and liquid crystal 1081. Integrated into the active matrix is a monolithic integrated circuit 100. In a preferred embodiment, the data scanner 120, the transmission gate 126, and the select scanners 130 are integrated onto the integrated circuit 100. In an alternative embodiment, the video interface 110, encoder 140, video polarity switch 150, temperature measurer 160, and light meter 170 are also integrated onto the integrated circuit 100. In addition, a sensor 950 (shown in phantom) can be integrated into the active matrix adjacent to the pixel electrode 1065.

For reasons to be explained below, the integrated circuit 100 is connected to the end pixel elements 1047 of each row of pixels by an aluminum interconnect 1400. In a preferred embodiment, the aluminum interconnect 1400 is 750 microns long.

Because the integrated circuit 100 comprises dynamic shift registers and other optically sensitive components, the integrated circuit 100 must be shielded from exposure to light 1101. A mechanical frame 1200 functions to shield the integrated circuit 100 from direct exposure to light 1101. The integrated circuit 100 must be formed far enough away from the active matrix region 90 so the mechanical frame 1200 is guaranteed to shield the integrated circuit 100. The 15 distance between the integrated circuit 100 and the active matrix region is dependent on the machined tolerances of the frame 1200 and mounting hole, and the tolerance of the glass size. A distance of about 750–1000 microns has been found to be sufficient.

Because of the relatively large distance between the integrated circuit 100 and the active matrix, an interconnect is required. The interconnect 1400 must also be shielded from incident light 1101. A shield layer 1500 formed by metallization deposition functions to shield substantially all of the interconnect 1400 from incident light 1101. In a preferred embodiment, the shield is formed a black matrix. The black matrix shield 1500 also functions to shield the integrated circuit 100 from exposure to collateral directed incident light.

Figure 9:
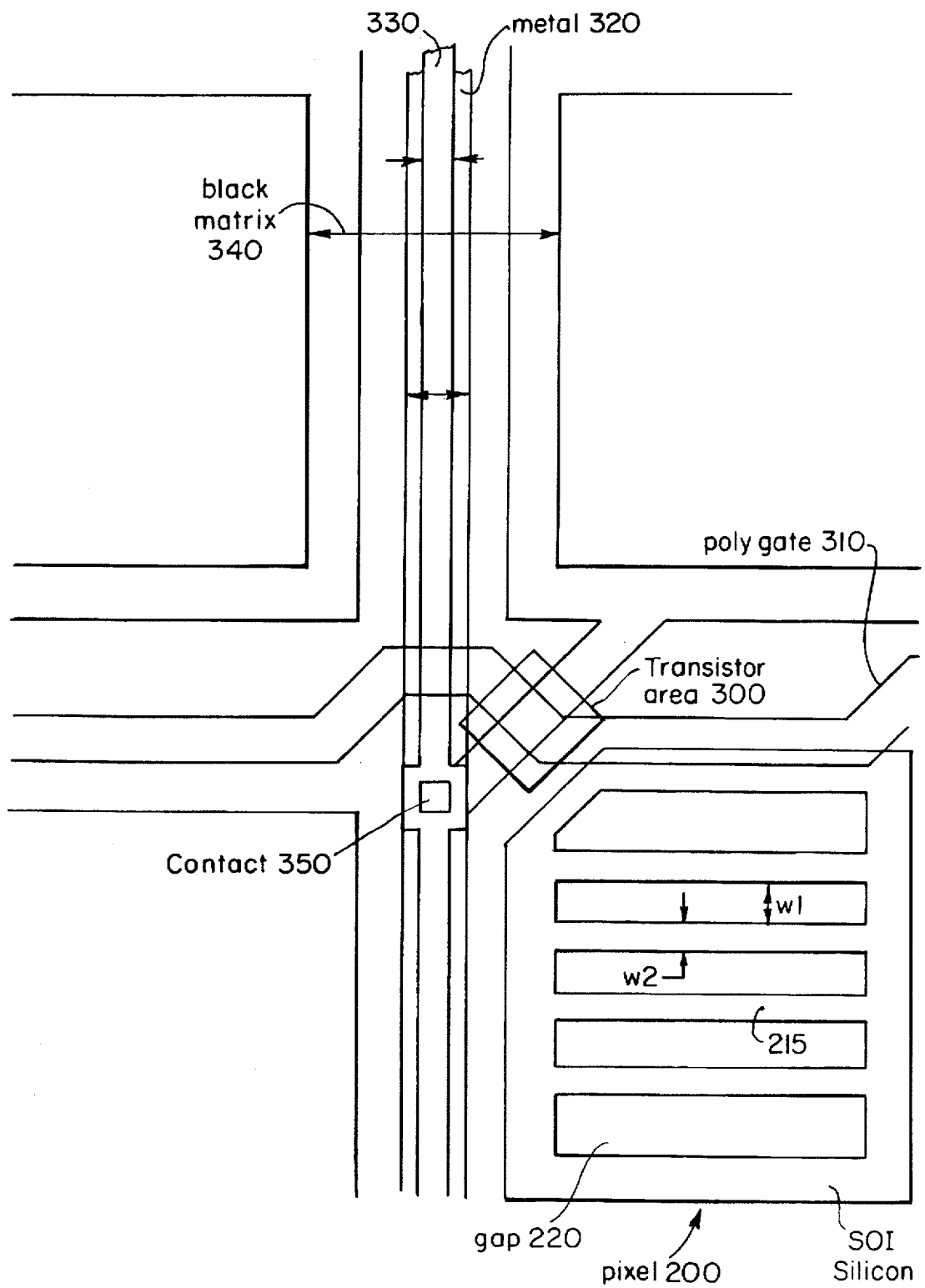
FIG. 9 is a partial cross-sectional view of a preferred active matrix display device illustrating a preferred shielding approach.

FIG. 9 is a schematic diagram of a partial pixel array of the active matrix. Generally, four pixel areas 1047 are shown. The silicon material is patterned to form an array of pixel electrodes and each electrode is further patterned into a grid, serpentine, or other suitable geometry to reduce transmission loss through the pixel electrode. The individual pixel electrode 210 initially comprises a solid layer of single crystal silicon. However, the element is processed such that areas 220 of silicon are removed and strips 215 of silicon remain. As such, the resulting pixel electrode 210 resembles a grid. The open areas 220 have a width (W1) of about 6 microns and the strips have a width (W2) of about 3 microns. In a preferred embodiment, there are four strips 215 and five removed areas 220 on the pixel electrode 210.

The grid provides an aperture through each pixel electrode 210 that improves transmission of light by reducing interference effects and also reducing reflection, absorption, and scattering caused by the pixel material. One advantage of the grid-shaped pixels is the increased light transmission through the active matrix, which results in brighter displayed images. Another advantage is that grid-shaped pixels minimize thickness variations in the single crystal silicon layer. These thickness variations cause light absorption or interference, which reduces the light transmission through the active matrix. By minimizing thickness variations, brighter displayed images can be provided.

Figure 10:
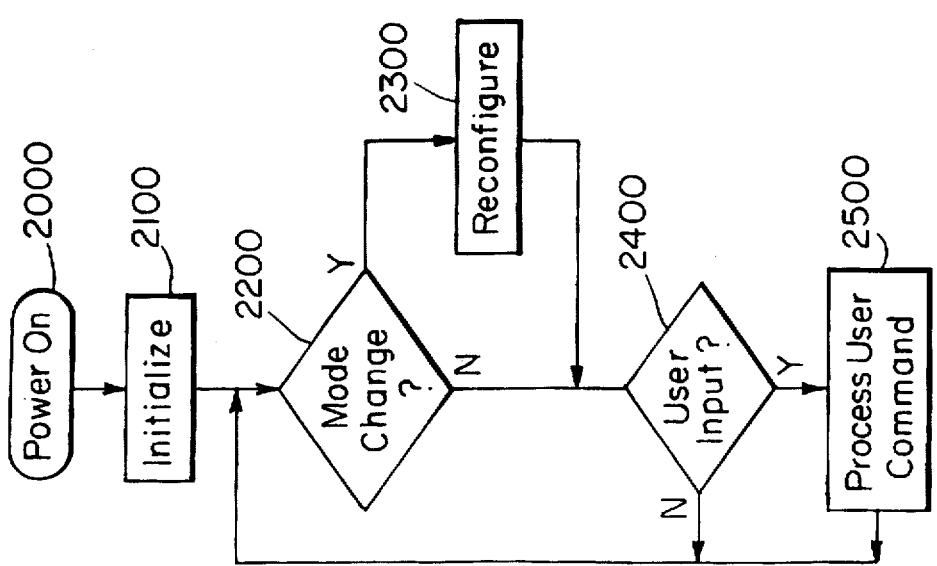
FIG. 10 is a flowchart of the processing steps of the control processor of FIG. 3A.

FIG. 10 is a flow chart of the processing steps of the control processor 112. The control processor is activated when the power is turned on as step 2000. Control then flows to step 2100, where the control processor performs initializations. These initializations include loading initial data into the FPGAs. Preferably, the initial settings are factory defaults. When configured with a VGA video connector, the factory default setting is 640H×480V graphics mode. When configured with a Macintosh™ video connector, the default settings are 640H×480V. The initialization procedure 2210 may also include a diagnostic self-test. After initialization is complete, control flows to a loop beginning at step 2200.

At step 2200, a check is performed on the video signal inputs to determine whether a mode change has occurred. If a mode change has occurred, control flows to step 2300. At step 2300, the FPGAs are reconfigured to reflect the current video mode. If there is no mode change at step 2200 or after reconfiguring at step 2300, control flows to step 2400.

At step 2400, a check is performed to determine whether there are any user inputs. If there are user inputs, control flows to step 2500. At step 2500, the user commands are processed. The user inputs can include mouse functions, brightness adjustments, contrast adjustments, tuning adjustments, frame adjustments, configuration saves, configuration resets, and a graphics/text mode selection (VGA modes only). After the user commands are processed at step 2500, or if there were no user input pending at step 2400, control flows back to the beginning of the loop at step 2200.

Figure 11A:
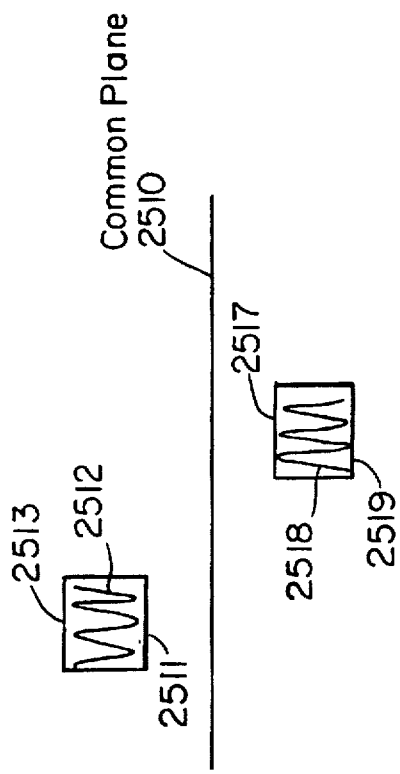
FIGS. 11a–11b a timing diagrams for driving the active matrix 90.

The brightness and contrast adjustments are provided to a digital-to-analog converter 50. The digital to analog converter 50 provides the contrast signal on signal line 51 and the brightness signal on signal line 53. The operation of the brightness and contrast adjustments will now be described with reference to FIG. 11A, which illustrates two columns of select data.

The video image is computed relative to a common plane voltage 2510, which is +9 volts in a preferred embodiment of the invention. The video signal 2512, 2518 is bounded by a white level 2511, 2517 and a black level 2513, 2519. As illustrated, the display is a drive-to-black active matrix display. The operation of a drive-to-white active matrix display is similar. The normal signal 2512 is centered about +15 volts with a range from 11.5 volts to 16 volts. The inverted signal 2518 is centered about +3 volts with a range extending from 2.5 volts to 4.5 volts.

Contrast is a direct control of the video input amplifier 152. When contrast is increased, the difference between the black signal level and the white signal level is increased such that there is less resolution per video data bit. When contrast is decreased, the difference between the black signal level and the white signal level is decreased such that he resolution per video data bit is increased.

Brightness controls the video input stage and determines the overall saturation of the data in a drive-to-black active matrix display. An increase in brightness decreases the difference between the common plane voltage 2510 and the white signal levels 2511, 2519 such that the center voltages are driven nearer to the common plane voltage 2510. A decrease in brightness separates the center voltages further from the common plane voltage 2510. The opposite is true in a drive-to-white active matrix display.

Figure 11B:
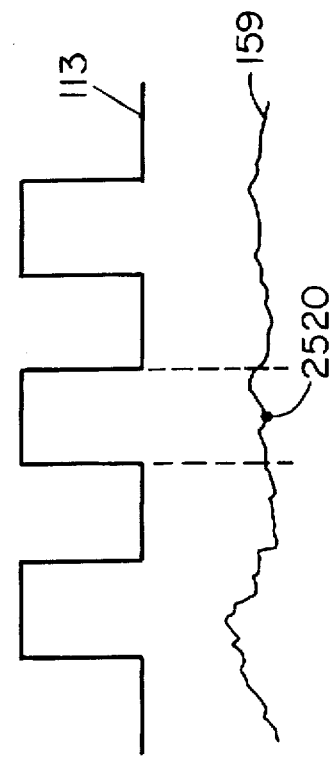

The operation of the pixel fine tuning adjustment will be described referring to FIG. 11B. The fine tuning adjustment adjusts the sampling point to provide for a stable, locked display. The analog signal 159 must be aligned with the pixel clock 113 such that the portion of the analog signal representing the pixel value 2520 is centered on the pixel clock 113. The fine tuning adjustment shifts the pixel clock forward or backward in time by fractions of a pixel.

The graphics/test mode switch toggles between graphics and text mode in VGA-based computers. In VGA-based computers, it is impossible to distinguish between text mode (740H×400V), which is typically used whenever the user is at a MS-DOS prompt, and the 640H×400V graphics mode. The video signals appear identical, although they are not. Unfortunately, the display must be informed of which mode the VGA is operating so data may be sampled correctly. When toggled to text mode, every ninth pixel is dropped so the 720 horizontal pixels can be represented in a 640 pixel display. The graphics/text mode button is only active when operating in either of the two applicable video modes.

The frame adjustment moves the display left or right by whole pixels or up and down by one scan line. The delay between scanner data and the horizontal sync and vertical sync signals is changed by the frame adjustment control. In a preferred embodiment of the invention, the available range is ±32 pixels horizontally and ±75 lines vertically.

The reset command causes the control system to be re-initialized to factory presets. The save command causes the currently active user configuration to be saved for the current video mode.

FIGS. 12A–12B are timing diagrams for a particular preferred embodiment of the invention.

FIG. 12A is a horizontal signal timing diagram illustrating the pixel clock signal 113, the pixel data signal 111, and the video data signal 159. The pixel clock signal 113 has a clock high width tDCH and a low width tDCL. The pixel data signal 111 has a pulse width tDPW that is triggered by the rising edges of the pixel clock signal 113. The rising edge of the pixel data pulse is delayed a time tHP from a rising edge of the pixel clock signal 113. The falling edge of the pixel data pulse is delayed a time tDP from the next rising edge of the pixel clock signal 113. The pixel data pulses have a horizontal pulse period tHPD. The time from the pixel data pulse to the first data valid is defined as tDV. Table VIII provides horizontal timing parameters.

TABLE VIII

HORIZONTAL TIMING

| Parameter | Meaning | Min | Typical | Max |
|---|---|---|---|---|
| tDCH | Clock High Width | 30 ns | | |
| tDCL | Clock Low Width | 30 ns | | |
| tDPW | DPulse Width | 60 ns | | |
| tHP | Clock to Pulse High | tDCH - 16 ns | tDCH | tDCH + 16 ns |
| tDP | Clock to Pulse Low | tDCH - 16 ns | tDCH | tDCH + 16 ns |
| tHPD | Horizontal Pulse Period | 19.2 μSecs | | |
| tDV | Pulse to first data valid | | 60 ns | 75 ns |

FIG. 12B is a vertical signal timing diagram, illustrating the select clock signal 117 and the select data signal 119. The select clock signal 117 has a clock high width tSCH and a clock low width tSCL. Table IX provides vertical timing parameters.

TABLE IX

VERTICAL TIMING

| Parameter | Meaning | Min | Typical | Max |
|---|---|---|---|---|
| tSCH | Clock High Width | 5 μS | 32 μS | |
| tSCL | Clock Low Width | 5 μS | 32 μS | |
| tSPW | SPulse Width | 5 μS | | |
| tHP | Clock to Pulse High | 14 nS | | 40 μS |
| tSP | Clock to Pulse Low | 14 nS | | 40 μS |
| tVPD | Vertical Pulse Period | 10.0 mS | 16.7 mS | |

Equivalents

While this invention has been particularly shown and described with reference and preferred embodiments thereof, it will be understood by those skilled in the art that various changes on form and details may be made therein without departing from the spirit and scope of the invention as defined by the appended claims.

What is claimed is:

1. A control apparatus for displaying a video signal from a video source using an active matrix liquid crystal display, the video source generating a select horizontal synchronization frequency from a plurality of selectable horizontal synchronization frequencies and a select vertical synchronization frequency from a plurality of selectable vertical synchronization frequencies, comprising a Silicon-on-Insulator (SOI) structure having a silicon device layer bonded to a transparent substrate by an adhesive layer, the active matrix liquid crystal display including an active matrix circuit formed in the SOI structure;

a video interface coupled between the video source and the display, the video interface generating a dot clock signal for driving the display at a fixed resolution in response to the select synchronization frequencies;

an active matrix interface circuit formed within the SOI structure and coupled to the video interface for actuating pixels of the active matrix circuit in response to the dot clock signal; and a user interface coupled between the video source and the video interface for enabling user control of the display.

2. The control apparatus of claim 1 wherein the video interface comprises a control processor and a dot clock regenerator, the control processor detecting a mode change in the video signal in response to a change in the select synchronization frequencies and signaling the mode change to the dot clock regenerator, the dot clock regenerator tracking changes in the select synchronization frequency in response to the mode signal from the control processor, the dot clock regenerator converting the select synchronization frequencies into the dot clock signal.

3. The control apparatus of claim 2 wherein the dot clock regenerator comprises a digitally programmable phase-locked loop for generating a dot clock that tracks changes in the select horizontal synchronization frequency, the mode change signal providing the digital programming.

4. The control apparatus of claim 3 wherein the digitally programmable phase-locked loop operates with a divider multiplication ratio substantially over 8:1.

5. The control apparatus of claim 4 wherein the divider multiplication ratio is about 800:1.

6. The control apparatus of claim 1 wherein the video interface is responsive to a select vertical synchronization frequency between about 56 and 70 Hz and a select horizontal synchronization frequency between about 15 and 35 Khz, and the fixed display resolution is 640H×480V pixels.

7. The control apparatus of claim 1 wherein the video interface is responsive to a select vertical synchronization frequency between about 56 and 100 Hz and a select horizontal synchronization frequency between about 15 and 66 Khz, and the fixed display resolution is 1024H×768V pixels.

8. A control apparatus for displaying an image encoded as a cathode ray tube (CRT) video drive signal from a video source using a transmissive active matrix display panel, the CRT video drive signal having a select vertical synchronization frequency from a group of selectable vertical frequencies, the apparatus comprising:

a silicon-on-insulator (SOI) structure including an active matrix circuit and an active matrix interface circuit within the display panel, the SOI structure being bonded to a transmissive substrate with an adhesive layer;

a video interface coupled between the video source and the active matrix interface circuit of the display panel, the video interface receiving the CRT video drive signal and in response generating an active matrix drive signal to actuate the display panel that generates the image.

9. The apparatus of claim 8 wherein the select vertical synchronization frequency is over 56 Hz.

10. The apparatus of claim 8 wherein the CRT video drive signal has a select horizontal synchronization frequency from a group of selectable horizontal frequencies.

11. The apparatus of claim 8 wherein the video source is a computer.

12. The apparatus of claim 8 wherein the video source includes a video port and the video interface includes a connector for coupling to the video port.

13. The apparatus of claim 8 wherein the display panel is a light transmissive light valve display panel.

14. A control apparatus for a projection display system, the display system displaying an image encoded as a cathode ray tube (CRT) video drive signal from a video source using a transmissive active matrix liquid crystal display panel, the CRT video drive signal having a select vertical synchronization frequency from a group of selectable vertical frequencies, the apparatus comprising:

a silicon-on-insulator (SOI) structure including an active matrix circuit an active matrix interface circuit within the display panel, the SOI structure being bonded to a transmissive substrate with an adhesive layer;

a video interface coupled between the video source and the display panel, the video interface receiving the CRT video drive signal and in response generating an active matrix drive signal to actuate the display panel to generate an image; and a light source that is optically coupled to the display panel to project the image onto a viewing surface.

15. The apparatus of claim 14 wherein the select vertical synchronization frequency is over 56 Hz.

16. The apparatus of claim 14 wherein the CRT video drive signal has a select horizontal synchronization frequency from a group of selectable horizontal frequencies.

17. The apparatus of claim 14 wherein the video source is a computer.

18. The apparatus of claim 14 wherein the video source includes a video port and the video interface includes a connector for coupling to the video port.

19. The apparatus of claim 14 wherein the CRT video drive signal is Red-Green-Blue encoded signal.

20. The apparatus of claim 14 wherein the CRT video drive signal is an analog signal.

* * * * *